ical Patent No.: US 9,770,195 B2
Date of Patent: Sep. 26, 2017

(12) United States Patent
Yaksh et al.

(54) AUTOMATED SCRATCH DETECTION SYSTEM AND SIGNAL PROCESSING ALGORITHM FOR THE STUDY OF PRURITUS IN ANIMALS

(71) Applicant: The Regents of the University of California, Oakland, CA (US)

(72) Inventors: Tony L. Yaksh, San Diego, CA (US); Shelle Malkmus, San Diego, CA (US); Marc Marino, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 193 days.

(21) Appl. No.: 13/963,981

(22) Filed: Aug. 9, 2013

(65) Prior Publication Data

US 2014/0046222 A1 Feb. 13, 2014

Related U.S. Application Data

(60) Provisional application No. 61/681,449, filed on Aug. 9, 2012.

(51) Int. Cl.
*A61B 5/11* (2006.01)
*A01K 29/00* (2006.01)

(52) U.S. Cl.
CPC .......... *A61B 5/1123* (2013.01); *A61B 5/1127* (2013.01); *A01K 29/005* (2013.01); *A61B 2503/40* (2013.01)

(58) Field of Classification Search
CPC .................................................. A01K 29/005
See application file for complete search history.

(56) References Cited

U.S. PATENT DOCUMENTS

| | | | | |
|---|---|---|---|---|
| 6,715,444 B1* | 4/2004 | Yabusaki | ............... | A01K 1/031 119/421 |
| 2003/0208335 A1* | 11/2003 | Unuma | ............... | A43B 3/0005 702/141 |
| 2003/0233041 A1* | 12/2003 | Yaksh | .................. | A61B 5/1105 600/409 |
| 2004/0245477 A1* | 12/2004 | Matsuda | ............... | A01K 29/005 250/458.1 |
| 2010/0310556 A1* | 12/2010 | Higuchi | ............. | C07K 16/2869 424/133.1 |
| 2010/0321189 A1* | 12/2010 | Gibson | ................ | A01K 29/005 340/573.3 |

OTHER PUBLICATIONS

Inagaki et al. ('Evaluation and Characterization of Mouse Scratching Behavior by a New Apparatus, MicroAct'; Skin Pharmacol Appl Skin Physio I 2003;16:165.*

(Continued)

*Primary Examiner* — Sean Dougherty
*Assistant Examiner* — Patrick Fernandes
(74) *Attorney, Agent, or Firm* — Gavrilovich, Dodd & Lindsey LLP

(57) ABSTRACT

The invention provides a method for automated assessment of pruritus comprising detecting movement of a band located on a limb of a subject animal so as to obtain a signal associated with the detection movement, processing the signal associated with the detected movement through an algorithm configured to establish a scratch movement trigger, and translating the processed signal into scratch counts.

20 Claims, 13 Drawing Sheets

(56) References Cited

OTHER PUBLICATIONS

Akiyama, Tasuku et al., "Transmitters and Pathways Mediating Inhibition of Spinal Itch-Signaling Neurons by Scratching and Other Counterstimuli," *PLoS ONE*, 2011, 6:e22665 (Exhibit 1).
Alemi, Farzad et al., "The TGR5 receptor mediates bile acid-induced itch and analgesia," *The Journal of Clinical Investigation*, 2013, 123:1513-30 (Exhibit 2).
Ayres, Samuel, "The Fine Art of Scratching," *JAMA*, 1964, 189:1003-7 (Exhibit 3).
Befus, A. Dean et al., "Mucosal Mast Cells: I. Isolation and Functional Characteristics of Rat Intestinal Mast Cells," *The Journal of Immunology*, 1982, 128:2475-80 (Exhibit 4).
Belghiti, Majedeline et al., "Molecular Bases of Disease: Potentiation of the Transient Receptor Potential Vanilloid 1 Channel Contributes to Pruritogenesis in a Rat Model of Liver Disease," *The Journal of Biological Chemistry*, 2013, 288:9675-85 (Exhibit 5).
Brash, H. M. et al., "A repetitive movement detector used for automatic monitoring and quantification of scratching in mice," *Journal of Neuroscience Methods*, 2005, 142:107-14 (Exhibit 6).
Carstens, Earl, "Scratching the Brain to Understand Neuropathic Itch," *The Journal of Pain*, 2008, 9:973-4 (Exhibit 7).
Cunha, Paulo Rowilson and Oswaldo Delfini Filho, "Pruritus: still a challenge," *An Bras Dermatol*, 2012, 87:735-41 (Exhibit 8).
Dahlberg, Gunnar, "Statistical Methods for Medical and Biological Students," *The British Medical Journal*, 1940, pp. 358-9 (Exhibit 9).
Dalgard, Florence et al., "Self-Reported Skin Morbidity among Adults: Associations with Quality of Life and General Health in a Norwegian Survey," *J Investig Dermatol Symp Proc*, 2004, 9:120-5 (Exhibit 10).
Davidson, Steve and Glenn J. Giesler, "The multiple pathways for itch and their interactions with pain," *Trends Neurosci*, 2010, 33:550-8 (Exhibit 11).
Davidson, Steve et al., "The Itch-Producing Agents Histamine and Cowhage Activate Separate Populations of Primate Spinothalamic Tract Neurons," *J Neurosci*, 2007, 27:10007-14 (Exhibit 12).
Davidson, Steve et al., "Relief of itch by scratching: state-dependent inhibition of primate spinothalamic tract neurons," *Nature Neuroscience*, 2009, 12:544-6 (Exhibit 13).
Elliot, G. R. et al., "An automated method for registering and quantifying scratching activity in mice: Use for drug evaluation," *Journal of Pharmacological and Toxicological Methods*, 2000, 44:453-9 (Exhibit 14).
Enerbäck, Lennart and Per M. Lundin, "Ultrastructure of Mucosal Mast Cells in Normal and Compound 48/80-treated Rats," *Cell Tiss Res*, 1974, 150:95-105 (Exhibit 15).
Fukamachi, Shoko et al., "Topical Cholecystokinin Depresses Itch-Associated Scratching Behavior in Mice," *Journal of Investigative Dermatology*, 2011, 131:956-61 (Exhibit 16).
Greaves, Malcolm W., "Itch in systemic disease: therapeutic options," *Dermatologic Therapy*, 2005, 18:323-7 (Exhibit 17).
Green, Amanda D. et al., "Influence of genotype, dose and sex on pruritogen-induced scratching behavior in the mouse," *Pain*, 2006, 124:50-8 (Exhibit 18).
Han, Sang-Kyou et al., "Phospholipase Cβ 3Mediates the Scratching Response Activated by the Histamine H1 Receptor on C-Fiber Nociceptive Neurons," *Neuron*, 2006, 52:691-703 (Exhibit 19).
Ikoma, Akihiko et al., "The neurobiology of itch," *Nature Reviews*, 2006, 7:535-47 (Exhibit 20).
Ikoma, Akihiko et al., "Anatomy and Neurphysiology of Pruritus," *Semin Cutan Med Surg*, 2011, 30:64-70 (Exhibit 21).
Inagaki, N. et al., "Evaluation and Characterization of Mouse Scratching Behavior by a New Apparatus, MicroAct," *Skin Pharmacology and Applied Skin Physiology*, 2003, 16:165-78 (Exhibit 22).
Inagaki, Naoki et al., "Participation of histamine $H_1$ and $H_2$ receptors in passive cutaneous anaphylaxis-induced scratching behavior in ICR mice," *European Journal of Pharmacology*, 1999, 367:361-71 (Exhibit 23).
Irman-Florjanc, Tatjana and F. Erjavec, "Compound 48/80 and substance P induced release of histamine and serotonin from rat peritoneal mast cells," *Agents and Actions*, 1983, 13:138-41 (Exhibit 24).
Ishii, Idaku et al., "Automatic Scratching Pattern Detection for Laboratory Mice Using High-Speed Video Images," *IEEE Transactions on Automation Science and Engineering*, 2008, 5:176-82 (Exhibit 25).
Jeffry, Joseph et al., "Itch Signaling in the Nervous System," *Physiology*, 2011, 26:286-92 (Exhibit 26).
Ji, Ru-Rong, "Recent progress in understanding the mechanisms of pain and itch," *Neurosci Bull*, 2012, 28:89-90 (Exhibit 27).
Johanek, Lisa M. et al., "A Role for Polymodal C-Fiber Afferents in Nonhistaminergic Itch," *J Neurosci*, 2008, 28:7659-69 (Exhibit 28).
Kawai, Taro and Shizuo Akira, "TLR signaling," *Seminars in Immunology*, 2007, 19:24-32 (Exhibit 29).
Kuraishi, Yasushi et al., "Scratching behavior induced by pruritogenic but not algesiogenic agents in mice," *European Journal of Pharmacology*, 1995, 275:229-33 (Exhibit 30).
LaMotte, Robert H. et al., "Mouse models of acute, chemical itch and pain in humans," *Exp Dermatol*, 2011, 20:778-82 (Exhibit 31).
Liu, Qin et al., "Sensory neuron-specific GPCRs Mrgprs are itch receptors mediating chloroquine-induced pruritus," *Cell*, 2009, 139:1353-65 (Exhibit 32).
Liu, Tong et al., "TLR3 deficiency impairs spinal cord synaptic transmission, central sensitization, and pruritus in mice," *The Journal of Clinical Investigation*, 2012, 122:2195-207 (Exhibit 33).
Liu, Tong et al., "Emerging role of toll-like receptors in the control of pain and itch," *Neurosci Bull*, 2012, 28:131-44 (Exhibit 34).
Marino, Marc et al., "Development and validation of an automated system for detection and assessment of scratching in the rodent," *J Neurosci Methods*, 2012, 211:1-10 (Exhibit 35).
Matterne, Uwe et al., "Incidence and Determinants of Chronic Pruritus: A Population-based Cohort Study," *Acta Dorm Venereol*, 2013, 93:532-7 (Exhibit 36).
Moser, Hannah R. and Glenn J. Gleiser, Jr., "Itch and Analgesia Resulting from Intrathecal Application of Morphine: Contrasting Effects on Different Populations of Trigeminothalamic Tract Neurons," *J Neurosci*, 2013, 33:6093-101 (Exhibit 37).
Nie, Yuman et al., "Real-time scratching behavior quantification system for laboratory mice using high-speed vision," *J Real-Time Image Proc*, 2009, 4:181-90 (Exhibit 38).
Nielsen, Ellen Holm and Jørgen Clausen, "Electron microscopic study of the regeneration in vivo of rat peritoneal mast cells after histamine secretion," *Cell and Tissue Research*, 1982, 224:465-8 (Exhibit 39).
Orito, K. et al., "A new analytical system for quantification scratching behaviour in mice," *British Journal of Dermatology*, 2004, 150:33-8 (Exhibit 40).
Oude Elferink, Ronald P. J. et al., "The Molecular Mechanism of Cholestatic Pruritus," *Digestive Diseases*, 2011, 29:66-71 (Exhibit 41).
Paus, Ralf et al., "Frontiers in pruritus research: scratching the brain for more effective itch therapy," *The Journal of Clinical Investigation*, 2006, 116:1174-85 (Exhibit 42).
Ringkamp, M. et al., "A role for nociceptive, myelinated nerve fibers in itch sensation," *J Neurosci*, 2011, 31:14841-9 (Exhibit 43).
Shim, Won-Sik et al., "TRPV1 Mediates Histamine-Induced Itching via the Activation of Phospholipase $A_2$ and 12-Lipoxygenase," *The Journal of Neuroscience*, 2007, 27:2331-7 (Exhibit 44).
Silva, L. L. et al., "Effects of *Lecythis pisonis* Camb. (Lecythidaceae) in a mouse model of pruritus," *Journal of Ethnopharmacology*, 2012, 139:90-7 (Exhibit 45).
Sugimoto, Yukio et al., "Effects of histamine $H_1$ receptor antagonists on compound 48/80-induced scratching behavior in mice," *European Journal of Pharmacology*, 1998, 351:1-5 (Exhibit 46).
Umeda, Koji et al., "A novel acoustic evaluation system of scratching in mouse dermatitis: Rapid and specific detection of invisibly rapid scratch in an atopic dermatitis model mouse," *Life Sciences*, 2006, 76:2144-50 (Exhibit 47).
Waxier, Beverly et al., "Primer of Postoperative Pruritus for Anesthesiologists," *Anesthesiology*, 2005, 103:168-78 (Exhibit 48).

(56) References Cited

OTHER PUBLICATIONS

Yaksh, Tony L. et al., "An automated flinch detecting system for use in the formalin nociceptive bioassay," *J Appl Physiol*, 2001, 90:2386-402 (Exhibit 49).
Yosipovitch, Gil et al., "Itch," *Lancet*, 2003, 361:690-4 (Exhibit 50).

\* cited by examiner

AUTOMATED SCRATCH DETECTION SYSTEM AND SIGNAL PROCESSING ALGORITHM FOR THE STUDY OF PRURITUS IN ANIMALS

This patent application claims the benefit of the filing date of U.S. Ser. No. 61/681,449, filed Aug. 9, 2012, the contents of all of which are herein incorporated by reference in their entireties into the present patent application.

Throughout this application various publications are referenced. The disclosures of these publications in their entireties are hereby incorporated by reference into this application in order to more fully describe the state of the art to which this invention pertains.

TECHNICAL FIELD

The present invention relates to pruritus research, and in particular, to the automated acquisition of scratching behavior in animals by detecting the movement of a lightweight, unrestrictive device that employs a validated detection algorithm negating the need for manual observation while maintaining accuracy in scratch counting.

BACKGROUND OF THE INVENTION

Pruritus, or pruritis, the unpleasant cutaneous sensation/itchiness that evokes a reflex behavior involving scratching directed at the skin, represents a significant clinical problem that has a very diverse etiology. Chronic pruritus can be manifested in 8-12% of the human population. Because of its clinical significance, mechanisms of pruriception are an important research topic. An important issue in advancing pruritus research is the development of a reliable and easily implemented method to assess hind paw scratching in animal, e.g., rodent, experimental models after exposure to a pruritic agent.

There are published strategies to assess rodent scratching. The most widely used strategy is manual counting through visual observation by a trained observer in real time or via recorded media. However, this process is subject to inter-observer bias and observer fatigue. Several automated systems have also been described. One such system involves processing videotaped behavior using motion detection software. This process requires specialized camera equipment and computer-intensive motion detection software. Another system involves the assessment of acoustic waveforms produced by paw movement. This system depends on eliminating external noise, and results in a lack of ability to determine the specific origin of the movement which evokes the sound. Yet another system involves assessing whole body movement using a strain gauge mounted cage. This system measures whole body activity, but not specifically homolateral paw movement. Still another system detects paw movement with a subcutaneous magnet, posing the need to implant a foreign body into a subject. Further still, detection, by a magnetic field, of movement of a ring attached to the lower leg (around the tibia just above the ankle) is also suggested, but can lead to limb swelling.

As seen from the aforementioned description, conventional systems for assessing itching employ labor-intensive visual counting either in real time or by media recording. While automated systems do exist, such systems proposed thus far are either extremely computer intensive (e.g., by requiring video analysis), non-selective (e.g., reliant upon body movement), invasive technologies (e.g., implanting subcutaneous magnets) and/or involve restrictive bands potentially impeding blood flow or causing localized inflammation (e.g., using constrictive bands).

SUMMARY OF THE INVENTION

Various embodiments described herein are directed to systems and methods that allow for the automated acquisition of scratching behavior in animals, including but not limited to, mice and rats. A system in accordance with various embodiments detects the movement of a lightweight, unrestrictive band placed on the limb of e.g., an unrestrained animal. The system employs a validated detection algorithm that minimizes the contribution of ambulatory behavior and matches the scratching counts that would be recorded by a trained human observer. Such a system in accordance with various embodiments allows for the concurrent assessment of multiple animals, and removes the need for a human observer. Therefore, observer error variance is reduced.

The invention provides a method for automated assessment of pruritus comprising detecting movement of a band located on a limb of a subject animal so as to obtain a signal associated with the detection movement, processing the signal associated with the detected movement through an algorithm configured to establish a scratch movement trigger, and translating the processed signal into scratch counts.

The invention also provides a system for automated assessment of pruritus comprising a computer, at least one testing chamber comprising transceiving antennas capable of creating and detecting fluctuations in an electromagnetic field, and a band configured for placement about a subject animal limb, wherein movement of the band perturbs the electromagnetic field resulting in an output signal processed by a scratch movement trigger algorithm via the processor, and wherein the processed output signal is displayed on the display and translated into scratch counts.

The invention also provides a method for determining whether an agent induces pruritus in a subject. The method comprises attaching a band to a limb of the subject. The method further comprises attaching a signal detection and processing device to the subject, the device being operatively connected to a memory device capable of storing retrieved signals and being able to detect motion of the band on the subject. Further, the method comprises detecting movement of the band on the subject that has been administered with the agent to obtain a signal associated with the detection movement. The movement may be a scratch movement to a predetermined area to which the agent has been administered on the subject. The method further comprises comparing the generated scratch counts to those generated from a nonpruritic agent, an increase indicating that the agent induces pruritus. The signal processing device comprises a processor configured to perform the steps of processing the signal associated with the detected movement through an algorithm configured to establish a scratch movement trigger; and translating the processed signal into scratch counts.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE INVENTION

Figure 1:
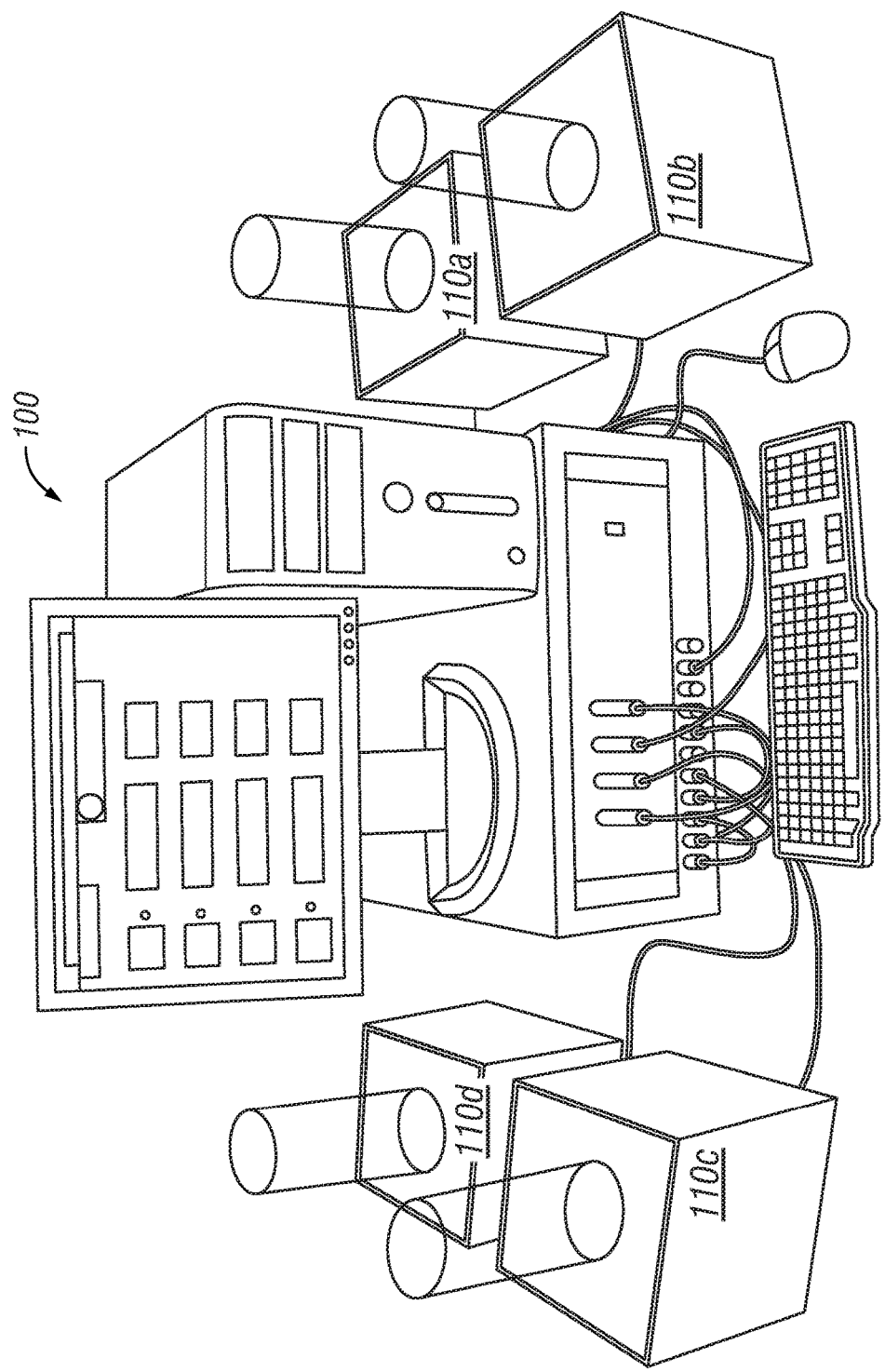
FIG. 1. A diagram showing an exemplary system organization of the PMD system 100 in accordance with various embodiments. As illustrated, there are 4 stations 110a-110d, each with a separate underlying pair of concentric antennas, the output of which are provided to a processor and are displayed on a computer screen.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b. Unless otherwise indicated, all numbers expressing quantities of ingredients, properties such as molecular weight, reaction conditions, and so forth as used herein, are to be understood as being modified in all instances by the term "about." Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The invention is a method and system for automated assessment of pruritus that uses the detection of the movement of a band located on any limb of a subject animal so as to obtain a signal associated with the detected movement. Such band may be made of any material, whether ferrous or nonferrous, capable of disturbing the electromagnetic field created by an electromagnetic transceiver in a testing area. Such disturbance creates a signal that is detected by another transceiver and is then displayed and processed through an algorithm configured to establish a scratch movement trigger that that distinguishes scratching movement from movement secondary to ambulation. Scratch movement triggers, or trigger signals, include machine detected movements configured to meet certain predefined thresholds for amplitude and duration to distinguish scratching movement of a limb from ambulatory movements or other non-scratching movements. Such scratch movement triggers are then translated into scratch counts, which each indicate a microburst or series of strokes occurring within a specified moving window time frame. For example, a microburst may include a high frequency scratching burst that indicates typical scratching response of a rodent or other pruritic animal that would be counted as one scratch by trained human observer. In an embodiment of the invention, these scratch counts, or microbursts, are the machine-determined equivalents to the "gold standard" of observed/visually reported scratch counts. The scratch movement triggers and scratch counts may be optionally stored in memory and then further processed into macrobursts, which indicate clusters of microbursts separated by periods of relative inactivity. In an embodiment of the invention, macrobursts, or macroburst patterns, are clusters of microbursts that indicate relatively high or low amounts of pruritic activity. For example, these macrobursts may enable the definition and quantification of the itch-scratch-quiescence cycle in pruritic animals, and are optimally calculated by using a fast Fourier transform (FFT) algorithm. The macroburst patterns can be analyzed to study the complex integration of pruritic input within the neural axis. By applying a potentially pruritic agent to a test subject and analyzing scratch counts, new pruritic agents may be discovered and macrobursts compared to study relative pruritic intensity. Alternatively, potentially antipruritic agents may be applied or mixed with known pruritic agents and tested for effectiveness for reducing pruritus.

Figure 2:
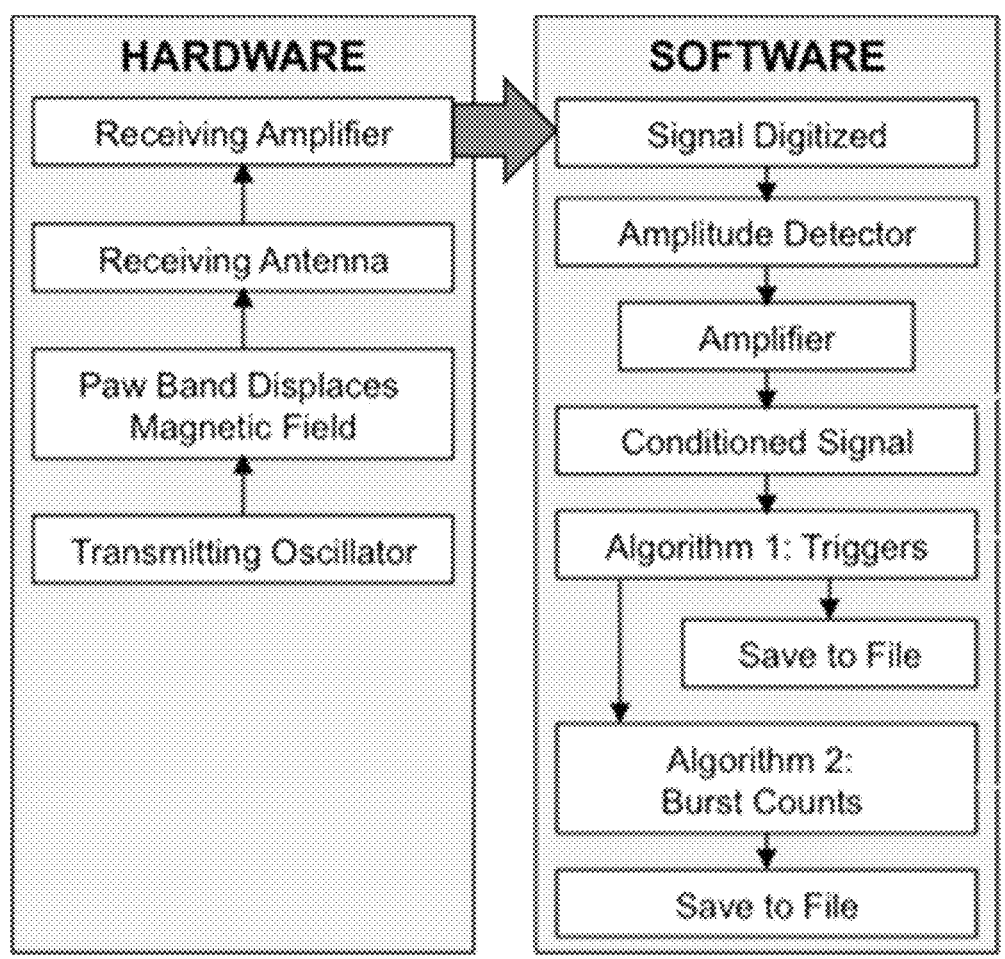
FIG. 2. An exemplary flow chart illustrating the signal processing data stream while schematically presenting the functions of the hardware and software of the PMD system.

The invention provides a method for automated assessment of pruritus. In one embodiment, the method is a computer implemented method. The method comprises detecting movement of a band located on a limb of a subject animal so as to obtain a signal associated with the detection movement. The subject animal may be one of any listed supra. The method further comprises processing the signal associated with the detected movement through an algorithm configured to establish a scratch movement trigger, e.g., as shown in FIG. 2. This processing may occur in real time or at a later time, and may be processed via hardware including but not limited to the National Instruments signal acquisition A-D converter system I6030 or PCI-M10-16Xe-10 and software such as the LabView software by National Instruments. The signal may be amplified, conditioned, and digitized, for example, at a sampling rate of about 1000 Hz at about 12-bit resolution. The signal may then be processed by an algorithm to detect peaks that indicate trigger signals. Further, the method comprises translating the processed signal into scratch counts. Scratch count may include a single microburst correlated to the gold-standard of a human-observed scratch from video observation. The algorithm used to produce scratch counts from scratch movement triggers may include but is not limited to any one of Algorithms A, B, or C as described in Table 1.

In one embodiment of the invention, the method further comprises transforming said scratch counts into macrobursts. The scratch counts may be transformed into macrobursts through an algorithm (e.g. a fast Fourier transform algorithm) configured to establish a macroburst. In another embodiment, the macrobursts may be used to define and quantify the itch-scratch-quiescence cycle in pruritic animals.

In another embodiment, the detection of the movement of the band may be performed by a receiving antenna capable of detecting perturbations within an electromagnetic field. A second transmitting antenna may generate this electromagnetic field and the band may interact with the field to produce signals that may be sensed by the receiving antenna.

In yet another embodiment, the method of the invention may further comprise analyzing macroburst patterns to study integration of pruritic input within a neural axis. For example, the neural axis may include but is not limited to the spinal dorsal horn, spinal cord or brain.

In one embodiment, the band comprises an unrestrictive and lightweight band. The band comprises any electromagnetically-sensitive ferrous or non-ferrous material (e.g. any non-ferrous metal, or plastics or other polymers that may be mixed with the electromagnetically-sensitive material).

In another embodiment, the scratch movement triggers may be saved as a file in a storage medium. In another embodiment, the scratch counts may be saved as a file in a storage medium. In another embodiment, the macrobursts may be saved as a file in a storage medium.

The invention also provides a method for determining whether an agent induces pruritus in a subject. The method comprises applying the agent to a selected or predetermined area of the subject and detecting movement of a band located on a limb of a subject animal to obtain a signal associated with the detection movement. The movement may be a scratch movement to the predetermined area on the subject. The method further comprises processing the signal associated with the detected movement through an algorithm configured to establish a scratch movement trigger. Further, the method comprises translating the processed signal into scratch counts and determining whether the agent induces pruritus by comparing the generated scratch counts to those generated from a nonpruritic agent, an increase indicating that the agent induces pruritus.

In another embodiment, macroburst patterns are saved to a file in a storage medium and analyzed to study integration of pruritic input within the neural axis. In another embodiment, scratch counts are saved to a file in a storage medium and analyzed to study integration of pruritic input within the neural axis. In another embodiment, scratch movement triggers are saved to a file in a storage medium and analyzed to study integration of pruritic input within the neural axis. Examples of storage mediums include but are not limited to a magnetic hard disk, optical disk, or solid state disk. Storage mediums could be physically attached to the computer, or connected via network or through the Internet.

The invention further provides a method for determining whether an agent reduces pruritus comprising determining whether an agent induces pruritus by mixing the agent with the pruritogen in varying amounts and repeating the method of the invention. The pruritogen is then compared to the generated scratch counts with those generated from a nonpruritic agent. An increase in pruritogen being indicative that the agent induces pruritus.

In one embodiment, the method further comprises transforming said scratch counts into macrobursts and comparing macroburst patterns to determine relative reduction of pruritic activity. The scratch counts may be transformed into macrobursts through an algorithm (e.g. a fast Fourier transform algorithm) configured to establish macroburst patterns. These macrobursts may be used to define and quantify the itch-scratch-quiescence cycle in various pruritic animals described supra.

In another embodiment, the detection of the movement of the band comprises detecting perturbations of an electromagnetic field created by movements of the band in a testing chamber and the scratch movement triggers are stored as a file in a storage medium. In another embodiment, the scratch counts are saved as a file in a storage medium. In another embodiment, the macrobursts are saved as a file in a storage medium.

The invention also provides a system for automated assessment of pruritus. The system may comprises a computer, at least one testing chamber comprising transceiving antennas capable of creating and detecting fluctuations in an electromagnetic field, and a band configured for placement about a subject animal limb such as a paw. The movement of the band perturbs the electromagnetic field resulting in a signal which is then processed by a scratch movement trigger algorithm via a processor, field programmable gate arrays (FPGA), or other digital or analog logic gate, and the processed signal may be optionally displayed on a display and translated into scratch counts using an algorithm such as Algorithm A, B, or C in Table 1.

In one embodiment, the computer includes a visual display device. This display can be a monitor, LCD panel, or any other visual output device capable of reproducing signals visually.

In another embodiment, the computer includes a storage medium onto which the raw signal (e.g., a digitized signal wave form), scratch movement triggers, scratch counts and macrobursts may be saved in separate files.

In another embodiment, the band comprises an unrestrictive and lightweight non-ferrous metal band. This band is capable of creating electromagnetic fluctuations or signals.

In another embodiment, the transceiving antennas comprise circular, concentric electromagnetic coils. The electromagnetic coils may be a pair of electromagnetic coils. The pair of electromagnetic coils comprises one larger diameter electromagnetic receiving coil and one smaller diameter electromagnetic transmitting coil.

In one embodiment, the electromagnetic coils may be positioned below the subject animal. In another embodiment, the coils may be positioned on the sides or above the subject animal.

In accordance with the practice of the invention, the limb may be a paw such as a hind limb paw or a fore limb paw of a subject animal. The subject animal may be a mouse, rat, squirrel, guinea pig, hamster, rabbit, shrew, mole, mink, cat and dog or any other animal having limbs and being used for pruritic analysis.

In one embodiment, the temporal resolution for a scratch count may be about 1 second. In another embodiment, the temporal resolution for scratch count may be anywhere from 0.5 to 1.5 seconds as in Algorithms A, B, or C of Table 1.

In one embodiment, the invention provides a method for classifying pruritogens eliciting similar scratch response by the method of the invention. The method comprises administering a pruritogen to one or more subject animals, determining number of scratch counts comprising automated assessment of pruritus, performing scratch counts over different doses of the pruritogen, and repeating the steps until all pruritogens to be classified have been examined. The method further comprises comparing scratch counts at a dose of a pruritogen or change in scratch counts at different doses or comparing a dose response curve of a pruritogen with other pruritogens, grouping pruritogens with similar scratch counts at the same dose or similar change in scratch counts as a function of pruritogen doses or with similar relative dose response curves in a single group, and creating as many groups of pruritogens as necessary to classify pruritogens that elicit similar scratch response.

In another embodiment, the invention provides a method for classifying pruritogens eliciting similar scratch response by the method of the invention. The method comprises administering a pruritogen to one or more subject animals, determining number of macrobursts for a certain duration, performing macroburst counts over different doses of the pruritogen and repeating steps until all pruritogens to be classified have been examined. The method further comprises comparing macroburst counts at a dose of a pruritogen or change in macroburst counts at different doses or comparing a dose response curve of a pruritogen with other pruritogens, grouping pruritogens with similar macroburst counts at the same dose or similar change in macroburst counts as a function of pruritogen doses or grouping pruritogens with similar relative dose response curves in a single group, and creating as many groups of pruritogens as necessary to classify pruritogens that elicit similar scratch response.

In another embodiment, the temporal resolution for a scratch count is about one second. Thus, a microburst of 2 or more scratches within about a second time frame results in one scratch count.

In another embodiment, the method for determining whether an agent causes pruritus may be used to determine whether a skin care product or regiment contains pruritic agents. This may be done by applying some of the product to a predetermined location on the subject and using the method of the invention to analyze any resulting pruritic activity.

In another, more mobile, embodiment of determining whether an agent induces pruritus in a subject includes the step of comparing the generated scratch counts to those generated from a nonpruritic agent, an increase indicating that the agent induces pruritus, the generating and detecting transceivers are located in a device attached to the subject in addition to the band on its limb. The device may also contain a processor capable of processing the signal into scratch counts and storage medium for saving the scratch counts.

The invention also provides a method for determining whether an agent induces pruritus in a subject. The method comprises attaching a band to a limb of the subject. The method further comprises attaching a signal detection and processing device to the subject, the device being operatively connected to a memory device capable of storing retrieved signals and being able to detect motion of the band on the subject. Further, the method comprises detecting movement of the band on the subject that has been administered with the agent to obtain a signal associated with the detection movement. The movement may be a scratch movement to a predetermined area to which the agent has been administered on the subject. The method further comprises comparing the generated scratch counts to those generated from a nonpruritic agent, an increase indicating that the agent induces pruritus. The signal processing device comprises a processor configured to perform the steps of processing the signal associated with the detected movement through an algorithm configured to establish a scratch movement trigger; and translating the processed signal into scratch counts.

The following examples are provided to further illustrate aspects of the invention. These examples are non-limiting and should not be construed as limiting any aspect of the invention.

EXAMPLES

Example 1

As alluded to previously, conventional systems for assessing itching employ labor-intensive visual counting, or computer-intensive automated systems that are non-selective with respect to assessed body movement or involve invasive technologies and/or restrictive bands which can potentially interfere with blood flow or cause localized inflammation. A paw motion detector (PMD) system in accordance with various embodiments of the present invention differs from the aforementioned current/conventional systems. First, the PMD system, in accordance with various embodiments permits continuous assessment, specifically, of movement of the homolateral hind paw. Second, the PMD system employs a minimally obtrusive, lightweight, and unrestrictive band. Third, the detection algorithm utilized by PMD system in accordance with various embodiments identifies a signal profile which distinguishes scratching movement from movement secondary to ambulation, and which matches manually observed scratch counts provided by a human observer.

The PMD system in accordance with various embodiments employs a small metal band placed on one hind paw of a subject, such as a rodent, that provides a signal through paw movement in an electromagnetic field. Additionally, a detection algorithm for scratching is utilized by the PMD system, where development of the detection algorithm resulted in the following observations. Unilateral SQ injection of Compound 48/80 (a polymer produced by the condensation of N-methyl-p-methoxyphenethylamine with formaldehyde that promotes histamine release and can be purchased from Sigma-Aldrich) into the lateral neck evoked periodic high frequency bursts of scratching at the injected site with the ipsilateral, but not the contralateral hind paw. Cross correlation between PMD and human observer counts after SQ 48/80 using the specified computational algorithm reveals a significant correlation. The signal to noise for 48/80 evoked scratching versus spontaneous activity (e.g., no pruritogen) is $\geq 6:1$.

Other findings include suggesting that the temporal resolution by the PMD system permits definition of two components. One component is a high amplitude component corresponding to the rapid discrete movement of the paw being lifted to the pruritic site (whereas analysis of hour-long epochs shows that microbursts are cyclically distributed in a lower frequency event termed macrobursts). Different pruritogens show different macroburst patterns. Additionally, SQ histamine and 48/80 produced dose dependent scratching reversed by diphenhydramine, and Chloroquine scratching displayed an inverse u-shaped dose response curve, which was insensitive to diphenhydramine. Further still, SQ 48/80 at intervals over 28 days showed no change in the scratching response within the same cohort of mice.

A power analysis showed 40% changes in scratching activity could be detected at the $p<0.05$ level with groups of 4 mice. Thus, the PMD system described herein can efficiently identify pruritogens and define the actions and pharmacology of pruritogenic agents. Accordingly, the PMD system in accordance with various embodiments is capable of specifically quantifying homolateral hind paw scratching with a degree of granularity that permits examination of microburst and macroburst patterns over extended periods of time initiated by known pruritogens with a counting covariance that matches the counting by a trained observer.

It should be noted that the automated PMD system in accordance with various embodiments is contemplated as being utilized to efficiently screen drug targets as antipruritics. Such targets include, but are not limited to, histamine H1 receptor, H4 histamine receptor, proteinase-activated receptor-2, serine proteases, cathepsin S, interleukin-31 (IL-31) receptor (such as gp130-like receptor), μ- (mu-), κ- (kappa-), δ- (delta-)opioid receptors, transient receptor potential vanilloid (TRPV) channels (such as TRPV 1 and 3 channels), cannabinoid receptor, nerve growth factor receptors (such as TrkA), endothelin receptors (such as ET-A and ET-B receptors), protease-activated receptors (PARs), calcitonin-gene-related peptide (CGRP) receptors, tropomyosin-related kinase A, acetylcholine receptors (such as M(3) muscarinic acetylcholine receptor), leukotriene B(4) receptor, autotaxin, rho-associated protein kinase (ROCK), gastrin-releasing peptide receptor (GRPR), Mas-related G-protein-coupled receptors (Mrgprs), neurokinin receptor-1 (NKR1), G-protein-coupled receptor TGR5, lysophosphatidic acid receptors (LPA receptors), substance P receptors (such as neurokinin 1 receptor), NK1 tachykinin receptors, BLT2 receptor, 12 (S)-lipoxygenase, and Toll-like receptors (TLRs, such as TLR7).

The PMD in accordance with various embodiments detects the movement of a non-ferrous metal band placed around one hind paw of a rodent (band weight=0.1 gram and 0.5 gram for mouse and rat respectively). The testing apparatus consists of cylindrical chambers (mouse: 8.5 cm diameter/22.5 cm tall; Rat: 15 cm diameter/30 cm tall). Under each cylinder is a pair of circular concentric electromagnetic coils, which serve respectively as antennas for transmission and reception. Outer coil diameters for the mouse and rat are 12 cm and 20 cm, respectively. The transmitter coil assembly is constructed to emit a 5-8 mW, 6-8 kHz, sinusoidal electromagnetic field (using, e.g., a Blue Max 800 Precision scan search coil from White's Electronics, Inc.) The detection principal is that eddy currents created by the movements of the ferrous and nonferrous metals perturb the EM field. Such perturbations produce an output waveform and are subsequently detected.

FIG. 1 is a diagram showing an exemplary system organization of the PMD system 100 in accordance with various embodiments. As illustrated, there are 4 stations 110a-110d, each with a separate underlying pair of concentric antennas, the output of which are provided to a processor and are displayed on a computer screen.

Figure 3:
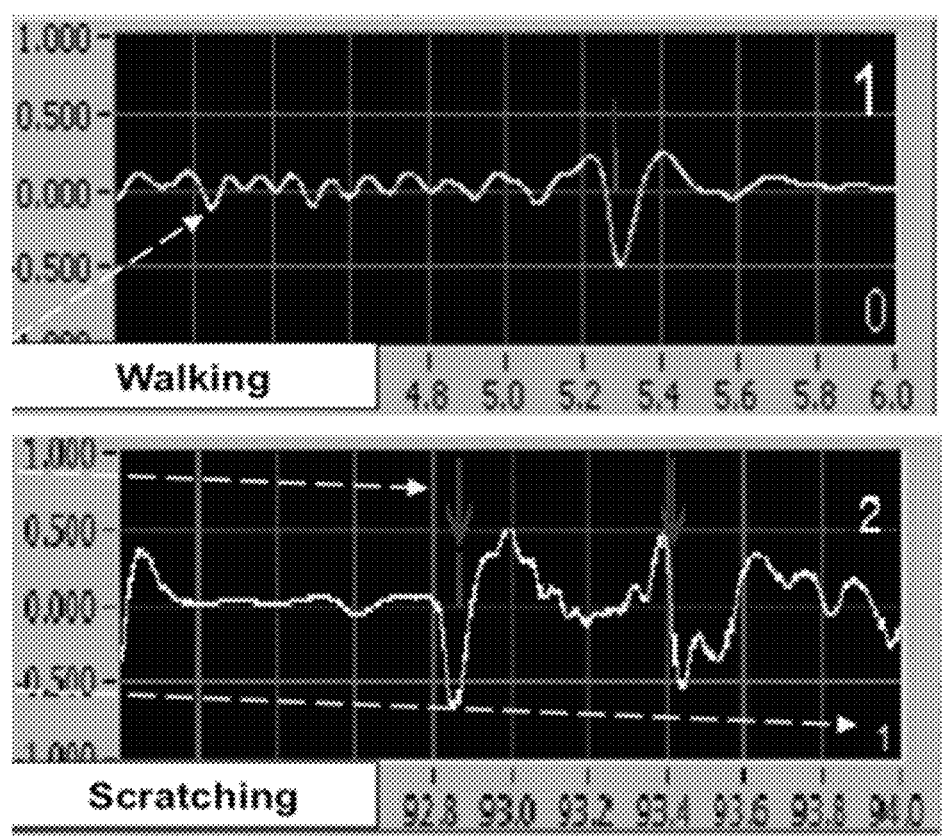
FIG. 3. An exemplary front panel view of the computer presentation for two channels. Each is a screen shot with a two second sequence showing a trigger generated by a walking step (top screen shot) and a scratch sequence (bottom screen shot). The smooth curve represents the conditioned signal, while the sharp vertical lines indicate the signal trigger provided by the first algorithm's analysis.

An analog signal from the sensing coil assembly is fed into a standard National Instruments® based signal acquisition A-D converter system (e.g., I6030 or PCI-MI0-16Xe-10 from National Instruments Corp.) driven into a standard LabView® based software (e.g., LabView v.5.1 from National Instruments Corporation). The signal is filtered, amplified, and digitized (sampling rate of 1,000 Hz, 12-bit resolution). This signal (shown in FIG. 3 and to be described in greater detail) is then entered and passed through a two component-triggering algorithm configured in the LabView® program. In the first phase, the processed signal is sent through an algorithm to establish a scratch movement trigger. In this phase, the processed signal is subjected to a "zero-crossing interval-peak height" analysis based on the signal amplitude in a sliding time window. The range of voltages (1 volt to 0.01 volt) over a moving 128-ms interval is configured to produce a continuous output waveform. This secondary waveform contains jagged peaks that correlate well with the scratch movement associated voltage transients found in the acquired waveform. The signal is then smoothed by using a non-weighted moving average filter. The smoothed range waveform is examined in real time by a peak-detection algorithm set to pick out spikes of >500 ms and amplitudes of >0.3 V. Each peak provided a trigger signal, which is represented by, e.g., line 310, 320, and 330 on the PMD system's display, as illustrated in FIG. 3. The signal is then processed through a second level algorithm to define bursting. A high frequency scratching burst, referred to herein as a microburst, is defined as multiple trigger signals occurring within a specified moving window time frame (e.g., 2 trigger signals within a 1.15 second time frame) without double counting trigger signals. As will be noted, systematic examination of these parameters was performed to define the optimal analytic configuration. These outputs correspond with the concurrent scratch counts provided by a trained human observer.

Paw movement events meeting the criteria of a scratch microburst are captured and summed at 1 minute increments by default (and can be summed from 1 second to 60 minute increments). Summed data is stored in compatible spreadsheets, such as Microsoft® Excel®. The LabView® programming provides 4 independent input-output channels, and presents the data for four animals simultaneously on the screen. The front panel includes the following in a file for each animal: 1) study/animal identifiers, treatment codes, dates, and other information relevant to the study; 2) a window displaying the previous 2 seconds of digitized signal (as shown in FIG. 3) with previously described markers indicating any flinch detection activity, and a count of the microbursts within that window; and 3) a line graph of each animal's trigger count by sampling interval (1 minute by default) since initiation of testing. The PMD system saves the following in two separate files: 1) the triggers produced by algorithm 1; and 2) the burst counts produced by algorithm 2. A typical view of the window displaying the digitized signal is shown in FIG. 3.

FIG. 2 is an exemplary flow chart illustrating the signal processing data stream for the PMD system schematically presenting the functions of the hardware and software.

FIG. 3 is an exemplary front panel view of the computer presentation for two channels. Each is a screen shot with a two second sequence showing a trigger generated by a walking step (top screen shot) and a scratch sequence (bottom screen shot). The smooth curve represents the conditioned signal, while the sharp vertical lines indicate the signal trigger provided by the first algorithm's analysis.

Since 2002 there have been over 6000 papers in published on pruritus, and as indicated previously, chronic pruritus is said to be manifested in at least 8% of the adult population. It is widely concluded that there have been few drugs to specifically target this problem, and there is a wide call to develop new drugs, requiring the pre-clinical assessment of drug targets as antipruritics. In the last 10 years there have been over approximately 400 papers examining pruritus in rodents. It is appreciated that the majority of this work employs the labor-intensive visual counting method described above in either in real time or by videotaping. This is time consuming, requires extensive training as well as validation of staff and subject. The PMD systems described herein address such issues.

REFERENCES FOR EXAMPLE 1

1. Inagaki N, Igeta K, Shiraishi N, Kim J F, Nagao M, Nakamura N, Nagai H. Evaluation and Characterization of Mouse Scratching Behavior by a New Apparatus, MicroAct. Skin Pharmacol. Appl. Skin Physiol., 2003; 16:165-75.
2. Orito K, Chida Y, Fujisawa C, Arkwright P D, Matsuda H. A new analytical system for quantification scratching behaviour in mice. Br. J. Dermatol., 2004; 150(1):33-8.
3. Ishii I, Kurozumi S, Orito K, and Matsuda H. Automatic Scratching Pattern Detection for Laboratory Mice Using High-Speed Video Images. IEEE Transactions on Automation Science and Engineering, 2008; 5(1):176-82.
4. Yuman N, Ishii I, Yamamoto K, Orito K, Matsuda H. Real-time scratching behavior quantification system for laboratory mice using high-speed vision. J. Real-Time Image Proc., 2009; 4:181-90.
5. Umeda K, Noro Y, Murakami T, Tokime K, Sugisaki H, Yamanaka K, Kurokawa I, Kuno K, Tsutsui H, Nakanishi K, Mizutani H. A novel acoustic evaluation system of scratching in mouse dermatitis: rapid and specific detection of invisibly rapid scratch in an atopic dermatitis model mouse. Life Sci., 2006; 79(22):2144-50.
6. Brash H M, McQueen D S, Christie D, Bell J K, Bond S M, Rees J L. A repetitive movement detector used for automatic monitoring and quantification of scratching in mice. J. Neurosci. Methods, 2005; 142(1):107-14.
7. Oude Elferink R P, Kremer A E, Martens J J, Beuers U H. The molecular mechanism of cholestatic pruritus. Dig. Dis., 2011; 29(1):66-71.
8. Elliott G R, Vanwersch R A, Bruijnzeel P L. An automated method for registering and quantifying scratching activity in mice: use for drug evaluation. J. Pharmacol. Toxicol. Methods, 2000; 44:453-9.
9. Marion, M, Haung, P, Malkmus S, Robert Shaw, E, Mac, E A, Shatterman, Y and Yaksh, T L. Development and validation of an automated system for detection and assessment of scratching in the rodent. Submitted.

Example 2

Material and Methods

All studies were performed according to protocols approved by the Animal Care and Use Committee of the University of California San Diego.

Animal Model

C57Bl/6 mice (male, 25-30 g, obtained from Harlan Sprague Dawley) were employed. Limited studies were also carried out in the rat (male Holtzman 250-300 g, obtained from Harlan Sprague Dawley).

To initiate scratching behavior, animals are shaven on the dorsolateral aspect of the neck and upper shoulder. The detection band is placed around the hind paw (e.g., over the metatarsals and distal tarsals) ipsilateral to the shaven area. Animals are then adapted to the testing chambers for one hour. To initiate scratching behavior, a subcutaneous (SQ) or intradermal (ID) injection of the pruritogen is made in the middle of the shaven area of skin using a 30 gauge needle. Data acquisition is then initiated.

Drugs

In the present studies, drugs were delivered in 0.1 mL volumes. Drugs employed were Histamine dihydrochloride (0.111, 1.110, 11.100 g/mL), chloroquine (0.1, 0.5, 2 mg/mL), 48/80 for the mouse (0.125, 0.25, 0.5, 1 mg/mL), 48/80 for the rat (1, 5, and 10 mg/mL) and Diphenhydramine given systemically (0.1, 0.3, 1 mg/kg). All drugs were prepared for delivery in saline (0.9%), and were obtained from Sigma-Aldrich.

Paw Motion Detector (PMD)

Physical Specifications.

The PMD detects the movement of a non-ferrous metal band placed around one hind paw of the rodent (for the mouse the band weight=0.1 g while for the rat the band weight=0.5 g). There are two distinct bands one for the rat and one for the mouse (see the band in Yaksh et al., 2001). The testing apparatus consists of cylindrical chambers (mouse: 8.5 cm diameter/22.5 cm tall; rat: 15 cm diameter/30 cm tall). Under each cylinder is a pair of circular concentric electromagnetic coils, which serve respectively as antennas for transmission and reception. Outer coil diameters for the mouse and rat are 12 cm and 20 cm, respectively. The transmitter coil assembly is constructed to emit a 5-8 mW, 6-8 kHz, sinusoidal electromagnetic field (Blue Max 800 Precision scan search coil White's Electronics, Inc., OR). The detection principal is that Eddy currents created by the movements of the ferrous and nonferrous metals perturb the EM field. Such perturbations produce an output waveform and are subsequently detected (Yaksh et al., 2001).

Signal Conditioning.

The analog signal from the sensing coil assembly is fed into a standard National Instruments based signal acquisition A-D converter system (I6030 or PCI-MI0-16Xe-10 National Instruments Corp.) driven into a standard LabView based software (Lab view v.5.1 National Instruments Corporation, Austin, Tex.). The signal is filtered, amplified, and digitized (sampling rate of 1000 Hz, 12-bit resolution). This signal (conditioned signal in FIG. 2) is then entered and passed through a two component-triggering algorithm configured in the Lab view program.

In the first phase, the processed signal is sent through an algorithm to establish a scratch movement trigger. In this phase, the processed signal is subjected to a "zero-crossing interval-peak height" analysis based on the signal amplitude in a sliding time window (see Yaksh et al., 2001). The range of voltages (1-0.01 V) over a moving 128-ms interval is configured to produce a continuous output waveform. This secondary waveform contained jagged peaks that correlated well with the scratch movement associated voltage transients found in the acquired waveform. The signal is then smoothed by using a non-weighted moving average filter. The smoothed range waveform is examined in real time by a peak-detection algorithm set to pick out spikes of >500 ms and amplitudes of >0.3 V. Each peak provided a trigger signal, which is represented by a red line on the automated system's display, see FIG. 3.

The signal is then processed through a second level algorithm to define bursting. A high frequency scratching burst, which we will now call a microburst, is defined as multiple trigger signals occurring within a specified moving window time frame (e.g. 2 trigger signals within a 1.15 s time frame) without double counting trigger signals. As will be noted, we systematically examined these parameters to define the optimal analytic configuration. We will show that these outputs correspond with the concurrent scratch counts provided by a trained human observer.

Data Collection.

Paw movement events meeting the criteria of a scratch microburst are captured and summed at 1-min increments by default (and can be summed from 1 s to 60 min increments). Summed data are stored in Microsoft Excel compatible spreadsheets. The LabView programming provides 4 independent input-output channels, and presents the data for four animals simultaneously on the screen. The front panel includes in the file for each animal: (1) study/animal identifiers, treatment codes, dates, and other information relevant to the study; (2) a window displaying the previous two seconds of digitized signal (as shown in FIG. 3) with previously described markers indicating any flinch detection activity and a count of the microbursts within that window; and (3) a line graph of each animal's trigger count by sampling interval (1 minute by default) since initiation of testing. The system saves in two separate files (1) the triggers produced by algorithm 1; and (2) the burst counts produced by algorithm 2. A typical view of the window displaying digitized signal is shown in FIG. 3.

Study Protocol

Model Optimization and Validation.

For validating studies, SQ injections in volumes of 0.1 mL of either vehicle (0.9% saline) or the itch-inducing agent 48/80 (0.5 mg/mL) were performed. A trained observer visually monitored the animal minute by minute for 60 min to provide a time locked assessment of scratching bursts. The visual observation of the scratching was defined as the application of the ipsilateral paw to the injection site followed by the appearance of high frequency movement of the paw across the injection site. Concurrently, the automated system recorded the unprocessed data for 60 min. Data was then analyzed by running the unprocessed trace through different algorithms. Observer counts and automated counts for each 10 min interval were plotted against each other. The best-fit regression lines were calculated.

Macroburst Analysis.

We sought to define and quantify the itch-scratch-quiescence cycle commonly seen in pruritic animals (Ikoma et al., 2006).

We observed clusters of microbursts (i.e. many distinct scratching movements over several minutes followed by several minutes of inactivity) in the histograms of individual animals. We defined these clusters of microbursts followed by a period of quiescence as a macroburst. The histograms of each individual animal's microbursts were transformed and then normalized minute by minute using a FFT algorithm ($1/\sqrt{4\pi Z^2}\Sigma e^{[-(t-t_i)^2]/2z^2}$) in order to differentiate peaks of scratching behavior from troughs of inactivity (Oppenheim and Schafer, 1999).

Homotopic Detection of Scratching Behavior.

To determine the ability of the system to show the homolaterality and site specificity of the detected scratching behavior, mice received SQ 48/80 on the same side to the banded paw and the opposite side to the banded paw.

Repeatability.

In order to assess the ability of the system to repeat results in the same animals over time we injected 4 mice with 48/80 and 4 mice with saline six times over a period of 28 days (day 0, 3, 7, 14, 21, 28).

Power Analysis.

Determination of power and minimum group size was accomplished using standard methodologies (Statsoft, Inc.). Data were used to undertake a power analysis and to predict nominal group sizes for assessing statistically significant changes in scratching activity.

Statistical Analysis

For assessment of the covariance between observer and machine counting with different trigger processing algorithms, the best fit regression line constrained to pass through 0 was calculated with 95% confidence intervals. Also, a correlation constant (R) was found for each line. This analysis was done for each individual animal, as well as for five animals pooled. Scratching analysis was accomplished by summing the total scores for a one hour period after pruritogen injection. These data were used to calculate mean and SEM or SD. Cross treatment comparisons were made with 1 way ANOVA with post hoc comparisons made using Bonferroni or an unpaired two-tailed t-test when comparing only two groups. For the study involving repeated injections a 2-way ANOVA with repeated measures with a post hoc comparison using Bonferroni was undertaken. For pharmacological data presented as a percent of control the standard error was estimated using the Doulborg formula standard error of quotients (Doulborg, 1940). Data analyses were performed using Prism (v.5).

Results

The following studies were undertaken to optimize and validate the model as well as to explain the system's development and functionality.

Comparison of Human Observation and PMD Counts

The SQ delivery of 48/80, histamine, and chloroquine to the dorsolateral neck resulted in vigorous scratching over a 60 min interval by the ipsilateral paw. Visual inspection revealed that this scratching behavior was characterized by brief bouts of high frequency application of the paw to the injected site (e.g. scratching microbursts).

Microburst Analysis.

Figure 4:
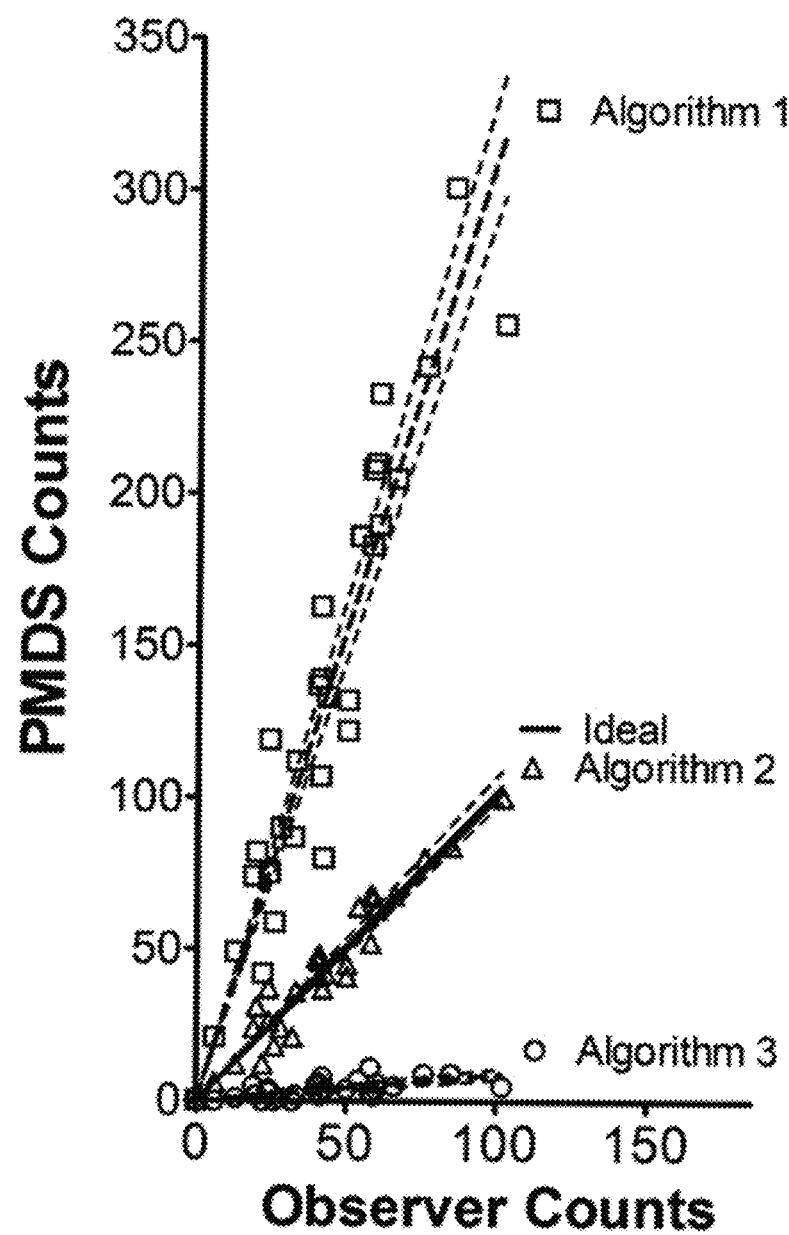
FIG. 4. Regression lines with 95% confidence intervals for cumulative microburst counts per 10 min intervals counted by the paw movement detection system plotted vs. the corresponding human count per 10 min intervals as a function of the algorithm used by the systems to count microbursts. Data for regression line of algorithm 2 for all 5 animals pooled: slope (mean±SEM)=1.022±0.024, CI (range)=0.9716 to 1.072, correlation constant (R)=0.964).

Counts of scratching microbursts were accumulated by an observer while concurrently acquiring the output from the paw motion detector for five mice. The output data was run through the PMD with counts being generated using three different microburst counting algorithms. The three described here were: (A) 1 trigger/1.15 s, (B) 2 triggers/1.15 s, and (C) 3 triggers/1.15 s. These algorithms are shown in FIG. 4 as algorithms 1, 2 and 3. For example in algorithm B, a microburst was counted if two triggers were observed within a 1.15 s interval. We separated the PMD observed microbursts and human observed scratching bursts over the sixty-minute period into six 10 min epochs. In FIG. 4, the microburst counts for each 10 min epoch as determined by the PMD for each algorithm were plotted versus human observer counts for the corresponding 10 min epochs. The calculated best fit regression line of the pooled data revealed that algorithm B yielded a regression line not statistically different from 1 with an R value of 0.964. Subsequently, we also plotted individual regression lines for each of the five mice separately. Again, PMD counts and human observer counts were compared in ten minute epochs over the 60 min. The mean and SD of the five slopes of the linear regression lines calculated for algorithm B was 1.025±0.026 with an average correlation coefficient (R) of 0.972 (see Table 1). Thus, the best correlation of automated scratching counts with human observer scratching counts for the three algorithms shown here was produced by algorithm B.

TABLE 1

Mean of the slope (slope ± SD), confidence intervals (CI range), and mean of the correlation coefficient (R ± SD) of the 5 separate linear regressions calculated for the 5 mice.

| Line | Slope $\mu \pm \sigma$ (n = 5) | 95% CI of slopes | R $\mu \pm \sigma$ (n = 5) |
|---|---|---|---|
| Perfect line | 1.000 ± 0.000 | 1.000 to 1.000 | 1.000 ± 0.000 |
| Algorithm A (1) | 3.125 ± 0.241 | 2.826 to 3.425 | 0.924 ± 0.052 |
| Algorithm B (2) | 1.025 ± 0.048 | 0.966 to 1.084 | 0.960 ± 0.043 |
| Algorithm C (3) | 0.091 ± 0.038 | 0.043 to 0.139 | 0.681 ± 0.296 |

Figure 6:
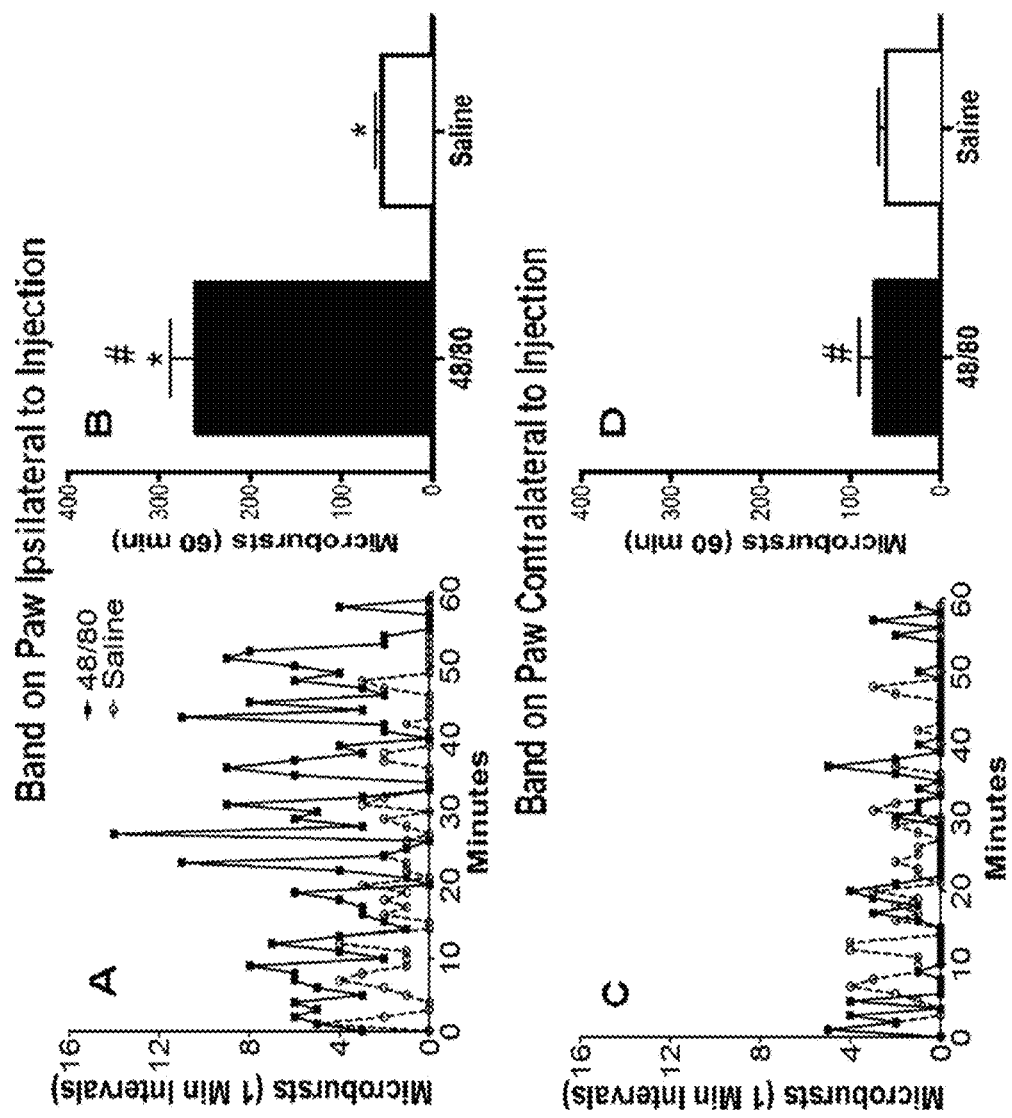
FIG. 6. (A) PMD microburst counts plotted vs. time after injection of 48/80 (0.5 mg/mL) or saline into single mice with the detection band ipsilateral to the injection site (N=1 for both as representatives of the mean). (B) Cumulative microburst counts (mean±SEM) over 1 hour after the SQ injection of 48/80 (N=5) or saline (N=5). (C) Same as A except detection band was placed on contralateral hind paw. (D) Same as B, except detection band was placed on contralateral hind paw (n=4) 2-tailed t-test: *p<0.01 48/80 ipsilateral vs. saline; 2-tailed t-test: #p<0.001 48/80 ipsilateral vs. 48/80 contralateral. The difference between saline and 48/80 contralateral was not statistically significant p=0.51.

Using the optimal algorithm as defined, the time course of the scratching microbursts observed after subcutaneous 48/80 (0.5 mg/mL) and subcutaneous saline are presented in FIG. 6A for two representative mice. As indicated in the accompanying cumulative count histogram for a 1 hour period, 48/80 displayed a significantly greater count than did saline (i.e. background activity in the absence of scratching behavior) with a pruritogen to noise (control-no pruritogen) ratio of approximately 5 (FIG. 6B).

Macroburst Analysis.

Figure 5:
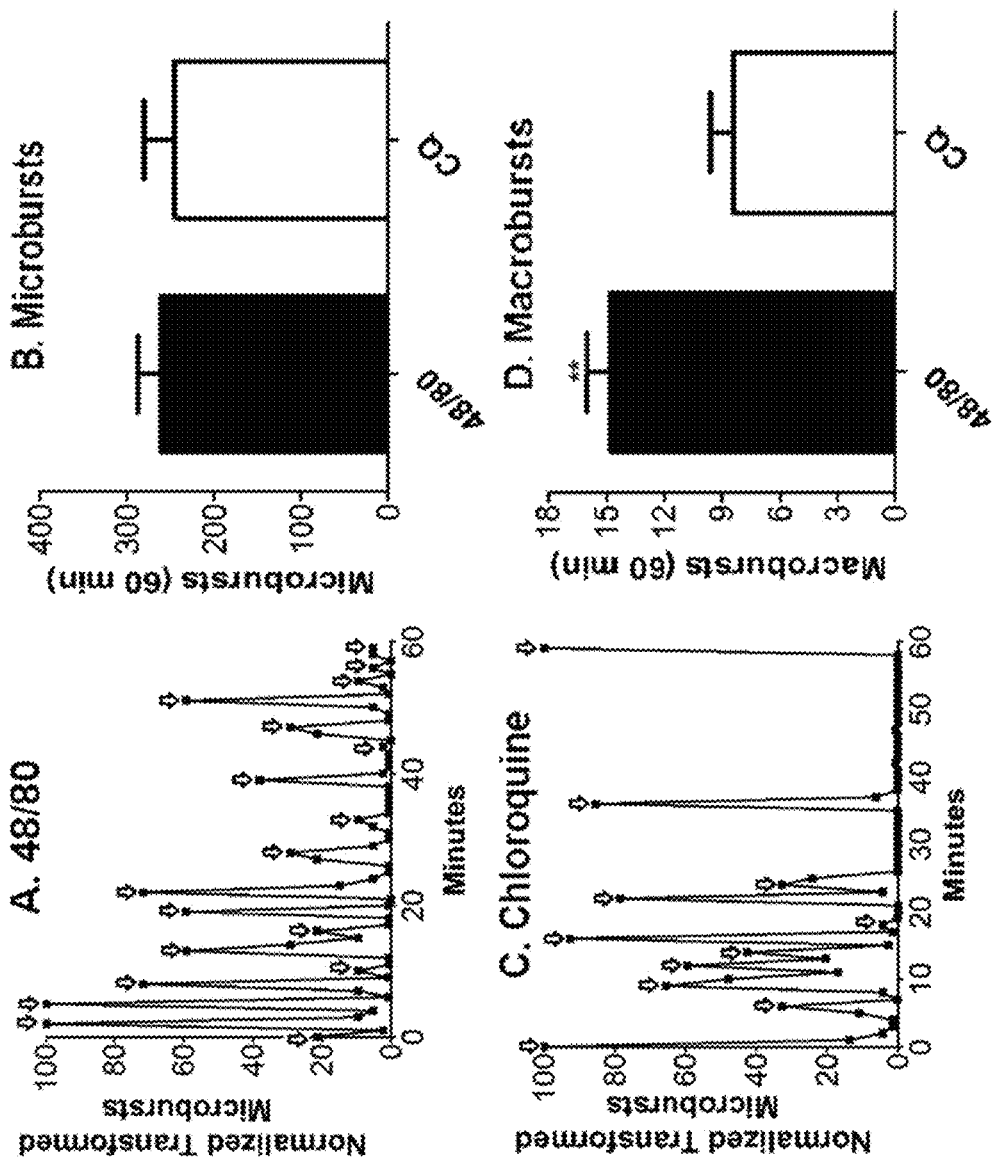
FIG. 5. (A) PMD transformed normalized microburst counts plotted vs. time after injection of 48/80 (0.5 mg/mL, N=1 representative of the mean). Each arrow represents 1 macroburst counted. (B) Cumulative microburst counts (mean±SEM) over 1 hour after the SQ injection of 48/80 (0.5 mg/mL, N=5) or chloroquine (1 mg/mL, N=5). Treatment groups were not significantly different. 2-Tailed t-test p=0.73. (C) Same as A except SQ chloroquine was injected (1 mg/mL, N=1 representative of the mean). (D) Cumulative macroburst counts (mean±SEM) over 1 hour after SQ injection of 48/80 (0.5 mg/mL, N=5) or chloroquine (1 mg/mL, N=5). Treatment groups were significantly different. 2-Tailed t-test: **p<0.001 48/80 macrobursts vs. chloroquine macrobursts.

Periods of high intensity scratching followed by intervals of inactivity or quiescence were typically observed in animals injected with pruritic compounds. To quantify the clustering of scratching behavior, we systematically defined a macroburst. Macrobursts are characteristic periods of intense scratching, which are quantified by an analysis of the clustering of microbursts. Each individual data point in a sixty-minute time course (the number of microbursts per minute) is inserted into the given fast Fourier transform (FFT) algorithm which produces a transformed number for each corresponding time point. The numbers were then normalized. The algorithm changes the data by minimizing and maximizing the data points' y values in order to make maximums farther from 0 and minimums closer to 0. This results graphically in major increases for periods where several minutes of contiguous high microburst counts appear, while several contiguous minutes of low or no microburst counts are decreased roughly to 0. These sixty minutes of new data points are then graphed using their corresponding unchanged x values. Each peak, (see arrows FIGS. 5A and 5C) again representing the maximized parts of the graph where microburst counts were high for several contiguous minutes, was counted as a macroburst. For comparison see FIG. 6A (48/80 normal 60 min time course of microbursts) to FIG. 5A (48/80 FFT transformed and normalized 60 min time course of macrobursts). The peaks were counted for each animal and averaged over five animals. While both agents at their respective SQ concentrations produced a similar overall microburst count (FIG. 5B), the respective macroburst analysis revealed distinguishable macroburst frequencies for the two agents (FIG. 5D). We observed for 48/80 an average of 14.8 macrobursts versus on average only 8.4 macrobursts for chloroquine.

Homotopic Detection of Scratching Behavior

To determine if the hind paw movement initiated by SQ 48/80 showed site specificity by being homolateral specific, the detection band was placed on the paw contralateral to the SQ injection site. As indicated in FIG. 6D, cumulative paw movement counts of the contralateral paw after contralateral 48/80 were not different from those observed after saline. Also, contralateral counts were significantly less than those observed when the ipsilateral paw movement was measured after the same dose of SQ 48/80 (FIG. 6B).

Repeatability

Figure 7:
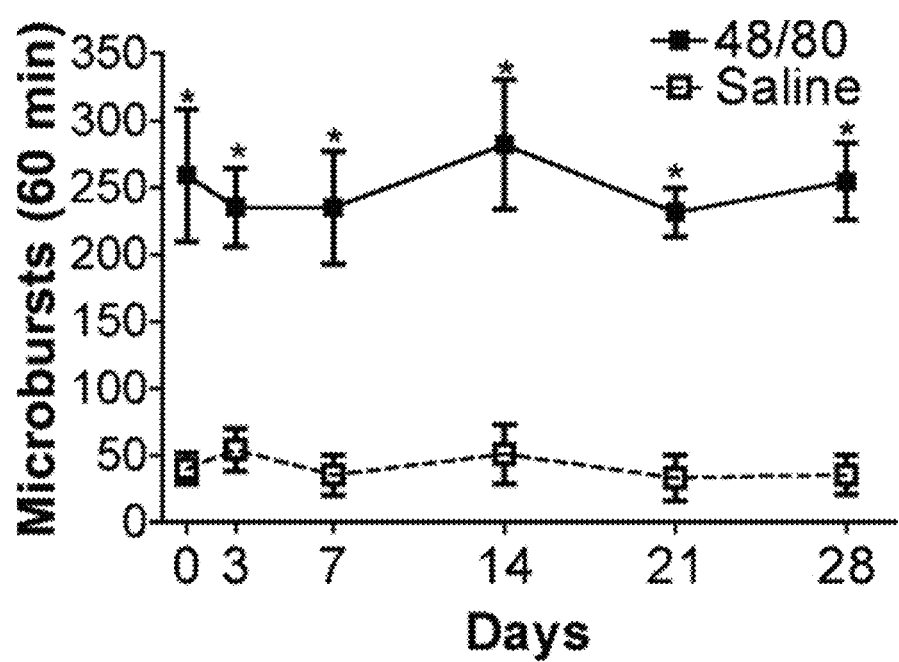
FIG. 7. Cumulative microburst counts (mean±SEM) during the hour after the SQ delivery of 48/80 (N=4) or SQ saline (N=4) given in the same animals periodically out to 28 days. 2-Way ANOVA repeated measures found an effect between treatment groups F(1,6)=70.82, p<0.001, indicating a significant difference between saline and 48/80 injected animals; an effective matching within treatment groups F(6,30)=2.81, p<0.027, indicating no significant difference between animals within each group respectively; no effect of time F(5,30)=0.46, p>0.80; no interaction between time and treatment groups F(5,30)=0.26, p>0.90. Thus, time did not change the outcome of the results for either treatment group respectively, nor did time interact with one treatment group differently than the other. Bonferroni post hoc saline vs. 48/80 groups at all time points, *p<0.001.

To determine response repeatability SQ 48/80 (0.5 mg/mL) or saline was given at intervals in the left dorsolateral neck periodically over 28 days and ipsilateral paw microbursts were counted. As indicated in FIG. 7, 48/80 resulted in a reliable increase over saline counts at all time points when assessed at intervals out to 28 days, with 48/80 vs. saline $F(1,6)=70.82$, $p<0.001$, and Bonferroni post hoc 48/80 vs. saline $p<0.001$ for all time points. There was no difference, however, between the individual mice within their respective treatment group, with matching within groups statistically significant, $F(6,30)=2.81$, $p<0.027$. No time effect or interaction was statistically significant with the 2-way ANOVA repeated measures. Thus, the microburst counts at all time points for each respective treatment group were not significantly different from each other.

Pruritogen Pharmacology

Using the algorithm defined above, we examined the effect of intradermal and subcutaneous pruritogens to assess the ability of the system to define scratching behavior in mouse and rat.

Histamine.

ID histamine resulted in a robust dose dependent scratching over a range of 0.111-11.1 g/mL. In support for the assertion that the SQ injection of histamine reflected a local afferent activation, injection of the local anesthetic lidocaine blocked the scratching behavior (FIG. 8A).

Chloroquine.

Figure 8:
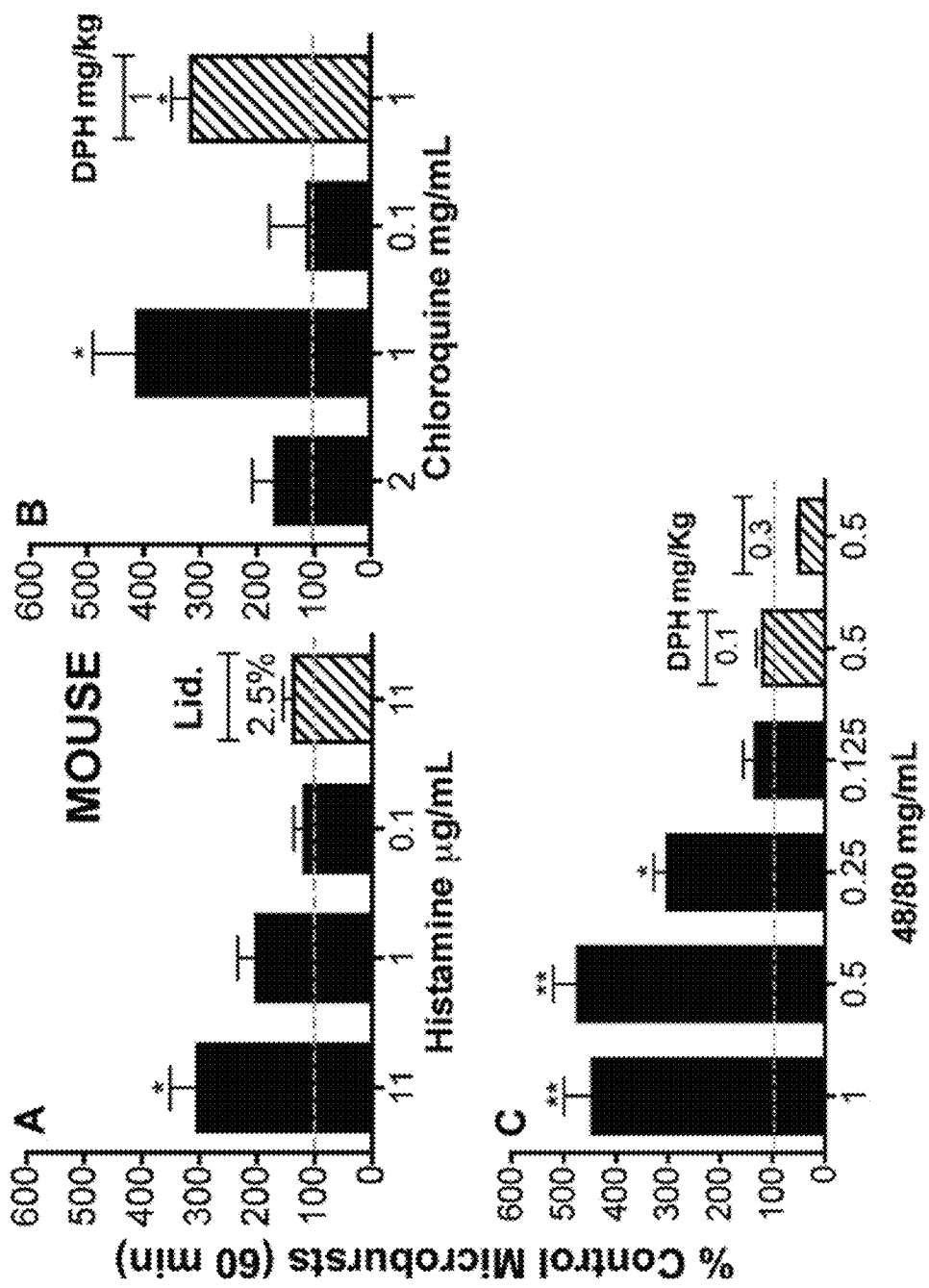
FIG. 8. Magnitude (mean±SEM) of cumulative scratching expressed as a percent of saline control at different doses of histamine, 48/80, chloroquine, DPH, or lidocaine (n=4 or n=5 for all groups). (A) SQ histamine alone or with SQ lidocaine (lid.) (2.5%) injected into the site 5 min prior to histamine. 1-Way ANOVA, Bonferroni post hoc vs. saline, p<0.01. (B) SQ chloroquine, 1-way ANOVA, Bonferroni post hoc vs. saline, p<0.01. SQ chloroquine (1 mg/mL) with pretreatment (30 min) of diphenhydramine (1 mg/kg, IP) 1-way ANOVA, Bonferroni post hoc vs. saline, p<0.01. (C) SQ 48/80, 1-way ANOVA, Bonferroni post hoc vs. saline, p<0.01 and *p<0.05. SQ 48/80 (0.5 mg/mL) with pretreatment (30 min) with increasing doses of IP diphenhydramine. 1-Way ANOVA, Bonferroni post hoc vs. saline **p<0.001.

The SQ delivery of chloroquine (0.1-2 mg/mL) resulted in a significant scratching incidence which was similar to that produced by the highest doses of histamine and 48/80 (FIGS. 8A and 8C). An inverse u shape dose response curve was observed (FIG. 8B). Diphenhydramine at 1 mg/kg had no statistically significant effect upon chloroquine (1 mg/mL) evoked scratching.

48/80.

SQ 48/80 produced a dose dependent scratching over a range of 0.125-0.5 mg/mL. The doses of 1 mg/mL and 0.5 mg/mL were not statistically different (FIG. 8C). In contrast to chloroquine, diphenhydramine, the H1 antagonist, resulted in a complete reversal of scratching produced by the highest dose of 48/80 at 0.1 mg/kg. Higher doses of diphenhydramine resulted in a suppression of behavior as compared to saline treated animals.

Rat

Figure 9:
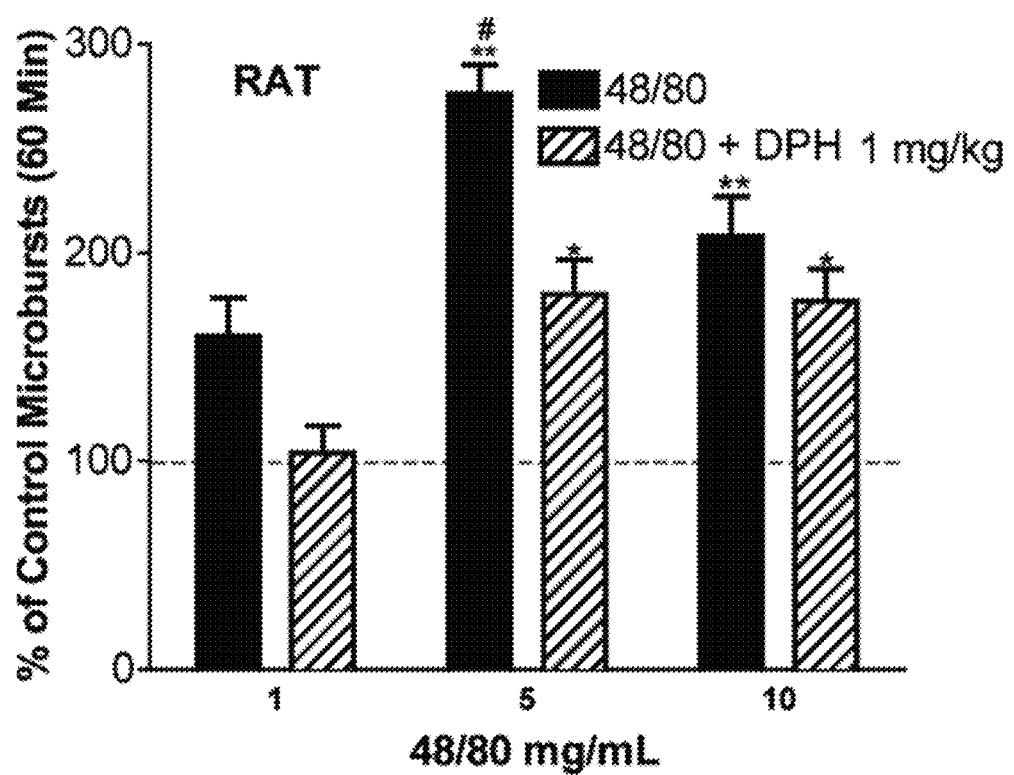
FIG. 9. Scratching in the rat. Magnitude (mean±SEM) of cumulative scratching expressed as a percent of saline control after SQ 48/80 at 3 doses either alone or with diphenhydramine. (1 mg/kg, IP, all groups N=3) 1 way ANOVA, Bonferroni post hoc 48/80 vs. saline, **p<0.01 and 48/80+DPH vs. saline, *p<0.05; Bonferroni post hoc 48/80 5 mg/mL vs. 48/80 5 mg/mL+1 mg/mL DPH, #p<0.05.

In parallel studies, we examined the effects of 48/80 on homolateral scratching behavior in the rat. As indicated in FIG. 9, SQ 48/80 resulted in an increase in scratching behavior at 5 mg/mL, but this increase was not present at 10 mg/mL indicating possible disruption of behavior because of systemically active concentrations. Alternatively, the mouse scratch detection algorithm may be optimized for the analysis of rat scratching behavior. As indicated, diphenhydramine resulted in a significant reduction in the observed magnitude of scratching (FIG. 9).

Power Analysis

Optimal group size based on a power analysis was calculated where the group mean and SEM for scratching in groups receiving a pruritogen (e.g. 48/80) would nominally be 258.8±24.8, with the minimum microburst score being 55.2±8.3 (as observed after SQ saline) (see FIG. 7). In screening work, we would wish to show a 50% reversal of the peak scratching response (50% of the difference between peak and baseline) over the baseline as compared to 48/80. For example: ([258.8−55.2]×0.7+55.2) versus 258.8±26.7. Thus, a score of 157 compared to 258.8, as calculated with a power=0.90 and an alpha=0.05 corresponds to a group size of 3. We would expect that with 3 animals, a 50% reduction in scratch counts using the PMD would be statistically significant at the $p<0.05$ level. Using similar calculations, it is indicated that 4 animals could show a 40% reduction, 8 animals a 30% reduction, and 16 animals a 20% reduction at the $p<0.05$ level.

Discussion

The broad clinical relevance of pruritus has led to an increasing interest in the development of mechanistic insights into its manifestation. The pharmacology of the systems underlying pruritus has grown increasingly complex. Aside from histamine mediated events, a variety of histamine independent mechanisms have now been identified, including MrgprA3, (a Mas-related G-protein-coupled receptor), GRPR signaling (gastrin-releasing peptide receptor, a metabotrophic receptor for the mammalian homolog of amphibian bombesin), and PAR (protease activated receptors activated by a variety of protease such as mucunain in cowhage) (see Jeffry et al., 2011). All of these systems have been shown to activate populations of sensory axons and discrete populations of dorsal horn neurons which carry information believed to be relevant to pruriception and its motor expression (scratching) (Davidson and Giesler, 2010).

An important component to such work is the development of preclinical surrogate models to permit study of drug effects. Such models depend upon the ability to reliably quantify the scratching induced by pruritogens. In the present work, we characterized the scratching behavior using a minimally invasive approach to capture unilateral hind paw movements evoked by SQ pruritogens injected into the back of the neck in mouse. Issues pertinent to the interpretation of these data will be considered below.

Observer Based Capture of Pruritic Activity

The gold standard of scratching behavior analyses is the observation of the behavior of the animal by a trained observer. Given the high frequency nature of this event, the typical approach is the review of video. Limitations to this approach are several. (i) Appropriate training of the observer requires time to teach the technique. (ii) Each observer should be cross correlated with results of the other observers to allow pooling of results by different observers. (iii) Because of the likelihood of systematic differences in observer scoring, in principle each observer should contribute data to all groups (to preclude a systematic data biasing secondary to such systematic difference between observers). (iv) The real time observations, even with speeded up video are tedious and the likelihood of observer fatigue must be considered when large numbers of records are being analyzed. (v) Finally, because the counts are subject to potential observer bias, all counting should be done without knowledge as to treatment. It should be noted that aside from blinding, we are aware of no published reports in the literature that systematically address these concerns regarding intraobserver reliability, interobserver correlation or temporal stability of the observer counting. Given these limitations of the observer based analysis of scratching, there has been an interest in developing and validating automated data collection and analysis systems. Validation of an indirect measurement system must include comparisons with the gold standard (i.e. real time human observer counting), assessment of the system's sensitivity, and a demonstration of its reliability.

Principle of the PMD

The present system employs detection of the displacement of a metal band in an EM field. The raw data output reveals a characteristic time variant signal with paw movement. The detection algorithms for a positive displacement of the paw must be able to distinguish a step, flinch, or scratching movements from each other. Assessment of the scratching wave produced by the band displacement in the PMD's EM field, however, has provided us with specific components that enable the development of an algorithm to identify scratching as a microburst while minimizing the contributions of grooming, walking and flinching behaviors.

Validation of the Scratching Detection by the PMD

Covariance of PMD Counts with the Human Observer.

The principal validation of the automated systems is based on the correlation of the machine counts with human observer counts assessed concurrently in mice displaying a pruritogen initiated scratching response. Here analysis on a mouse by mouse basis or analysis as a pooled group revealed a highly significant regression of the observer vs. PMD counts, producing a slope not significantly different from one with an R value of 0.964 (pooled) and 0.972 (mean of 5 R values from the 5 single mouse regressions). Cross validation between other automated data acquisition systems and observer counts have used similar statistical methods in order to confirm their systems' accuracy (Brash et al., 2005; Umeda et al., 2006).

Pharmacological Assessment.

Standard pruritogens, including histamine, 48/80, and chloroquine were observed in the present work to produce dose dependent increases in measured scratching in dose ranges that have been previously reported to be effective (Inagaki et al., 1999; T. Liu et al., 2012). 48/80 was seen to cause scratching in a dose dependent fashion, while scratching was attenuated in an equally dose dependent fashion with administration of diphenhydramine (Sugimoto et al., 1998). Chloroquine was seen to produce the widely reported inverse U shaped dose response curve (Green et al., 2006), and was shown to be diphenhydramine insensitive. Of importance and consistent with previous work, the pruritogenic effects of 48/80 but not chloroquine were shown to be effectively blocked in a dose dependent fashion by the antihistaminic diphenhydramine. Chloroquine treated animals given diphenhydramine had a lower mean microburst count than those treated with chloroquine alone, but this was not statistically significant. Chloroquine has been shown to degranulate mast cells, thus releasing some histamine, which would explain diphenhydramine's statistically non-significant effect (Q. Liu et al., 2009).

Our microburst counts closely mirror the observed scratch counts of other investigators using non-automated counting methods. Authors have found 48/80 produces a range of 135-480 scratch counts extrapolated to 60 min at similar doses to 1 mg/mL (Han et al., 2006; Silva et al., 2012; T. Liu et al., 2012). Our observed counts of 258.8±26.7 fall within this range. Our saline counts, however, appear to be higher than several published results 40-60 vs. 20-30 extrapolated over 60 min (Han et al., 2006). Other data have shown more variability. Shim reports in the same paper two groups of controls that scratched 7.2 bouts in 20 min (C57Bl/6J) while the other scratched 25 bouts in 20 min (ICR), which extrapolate to 20 for inbred and 75 for outbred scratch bouts per 60 min (Shim et al., 2007). Fukamachi reports untreated ICR mice scratching 40-50 times in 20 min (Fukamachi et al., 2011). Unfortunately, saline control results are not widely reported in most studies involving pruritus. The reported higher scratch counts were the specific controls used to compare against 48/80 only. The pooled saline data (n=28) had a mean of 39±19 (mean±SD), which suggests less of a difference from published data perhaps on the order of 10-15 scratch bouts over an hour, with no statistically significant difference. Differences in procedure and the fact that saline injected animals may produce more confounding behaviors because they are not occupied with scratching for the entire 60 min are other possible explanations for the observation.

Repeatability.

An important attribute of an automated test system is its reliability. Here we show that over a 28 day period the same mice maintain remarkable stability in their response to 48/80. This supports not only repeatability, of the system, but the ability to generate reliable data from the same animal with at least one pruritogen. Such a property is important for allowing the repeated use of the same animal such as a genetically modified mouse, which may have limited availability. For example, recent studies have shown using TLR knockout mice that the innate immune system plays an important role in the scratching behavior of mice (T. Liu et al., 2012). In the present study, we showed that 48/80 administered multiple times in a week, and once a week after the initial injections showed no statistically significant difference between time points in the number of scratches evoked. 48/80, however, is a mast cell degranulator (Enerback and Lundin, 1974; Befus et al., 1982; Irman-Florjanc and Erjavec, 1983). Nielsen described a decrease in the total number of granules in mast cells over an extended period of time in the rat (Nielsen and Clausen, 1982). The present behavioral data, however, suggests that the behavioral result (scratching) of SQ injection of 48/80 remained consistent. This may be a result of differences in physiology of the rat versus the mouse, or simply the fact that despite lower granule counts 48/80 still provides a robust behavioral effect with repeated injections at 1,3, and 7 day intervals.

Scratching Behavior Phenotype

Visual assessment of the locally evoked scratching behavior reveals two evident characteristics: a specific somatotopic response and a complex temporal profile.

Somatotopy.

After the local delivery of a pruritogen such as histamine or chloroquine, a homotopic scratching is observed, which we define as the targeted scratching behavior at the site of the pruritogen injection. The homotopic specificity demonstrated here by the PMD in regards to paw band placement and the drug delivery site is an important attribute in quantifying the behavior of scratching. Placement of the band contralateral to the injection site revealed a response index no different from the saline injected animal.

Temporal Profile.

Examination of the paw movement and the signal that it generates indicated that there are two components. Component one is a high amplitude component that corresponds to the rapid discrete movement of the paw being lifted to the pruritic site. This behavior is represented by a transient signal with a maximum 500 ms duration and amplitudes of >0.3 V (in this system). This characteristic constituted the basic trigger. Examining concurrent video records, however, revealed that the trigger properties were shared by motor components of walking and grooming. Accordingly, in the absence of a pruritogen, there is a high resting count of the trigger signal that reflects normal motor behavior in the rodent.

The second component of the scratching response is the appearance of several high frequency movements in a close sequence which correspond to the paw being rapidly moved across the pruritogenic site usually one, two, or three times followed by the paw's return to a rest position. It is this composite of movements, lifting the leg up, moving the paw across the pruritic area, and putting the paw back down that correspond to the scratch count reported by the observer. All three segments of scratching are taken into account by the algorithms in order to identify a waveform as a scratch. Thus, the system counts a microburst as the entire movement of the "scratch" from the initial lift of the leg to the pruritic site, to the movement of the paw across the pruritic site, and finally to the removal of the paw from the site. The waveforms produced by the various temporal components of scratching of the hind paw to the dorsolateral neck identified by the first algorithm causes the system to trigger at a specific frequency. Using an algorithm that produced a count based on 2 triggers per 1.15 s, which we defined as a microburst, we matched microbursts to the scratch counts of the trained observer.

The components of pruritogen evoked scratching were revealed in the analysis of hour long epochs. It was found that microbursts were cyclically distributed in a lower frequency event that suggests that these microbursts after 48/80 or chloroquine occur in clusters, which we termed macrobursts. These slower frequency macrobursts likely correspond to the itch-scratch-quiescence cycle (Ayres, 1964; Aoki, 2003) for a histamine dependent pruritic agent (48/80) and a histamine independent pruritic agent (chloroquine). Importantly, the differences in total scratch counts (microbursts) do not indicate the different patterns of scratch behavior between these agents. The ability to bin scratch bursts down to the second allows for an analysis of scratching behavior over the course of the treatment in a way that has not previously been undertaken in a behavioral model.

These binary periodicities in scratching activity, i.e. the animal either scratches in clusters or remains inactive, are intriguing as they likely reflect the properties of the underlying systems generating the scratch response. Recording from primary afferents after histamine (48/80) or histamine independent stimulus (such as cowhage or chloroquine) typically reveals such bursting behavior in small afferents (see for example Johanek et al., 2008; Ringkamp et al., 2011). In addition, there is evidence that the integration of pruritic input at the level of the spinal dorsal horn is subject to considerable modulation (Carstens, 2008; Akiyama et al., 2011). Properties of this periodicity in scratching as suggested by the present analysis may also reflect upon this central modulation (see for example Davidson et al., 2007, 2009). A combination of behavioral analysis with electrophysiology data will be of great interest in determining the periodic properties produced by the circuitry of pruriception.

REFERENCES FOR EXAMPLE 2

Akiyama T, Iodi Carstens M, Carstens E. Transmitters and pathways mediating inhibition of spinal itch-signaling neurons by scratching and other counterstimuli. PLoS One 2011; 6(7):e22665 [Epub 2011 Jul. 27].

Aoki T. 'Pleasure of scratch' is a complex sensation of itch and pain. In: 2nd international workshop for the study of Itch; 2003.

Ayres S J. The fine art of scratching. JAMA 1964; 189:1003-7.

Befus A D, Pearge F L, Jorewood P, Binenstock J. Mucosal mast cells. I. Isolation and functional characteristics of rat intestinal mast cells. J Immunol 1982; 128:2475-80.

Brash H M, McQueen D S, Christie D, Bell J K, Bond S M, Rees J L. A repetitive movement detector used for automatic monitoring and quantification of scratching in mice. J Neurosci Methods 2005; 142(1):107-14.

Carstens E. Scratching the brain to understand neuropathic itch. J Pain 2008; 9(11):999-1005.

Dalgard F, Svensson A, Holm J O, Sundby J. Self-reported skin morbidity among adults: associations with quality of life and general health in a Norwegian survey. J Investig Dermatol Symp Proc 2004; 9:120-5.

Davidson S, Giesler G J. The multiple pathways for itch and their interactions with pain. Trends Neurosci 2010; 33(12):550-8.

Davidson S, Zhang X, Yoon C H, Khasabov S G, Simone D A, Giesler Jr G J. The itch-producing agents histamine and cowhage activate separate populations of primate spinothalamic tract neurons. J Neurosci 2007; 27(37): 10007-14.

Davidson S, Zhang X, Khasabov S G, Simone D A, Giesler Jr G J. Relief of itch by scratching: state-dependent inhibition of primate spinothalamic tract neurons. Nat Neurosci 2009; 12(5):544-6.

Doulborg G. Statistical methods for medical and biological students. London: George Allen and Curwin Ltd; 1940.

Elliott G R, Vanwersch R A, Bruijnzeel P L. An automated method for registering and quantifying scratching activity in mice: use for drug evaluation. J Pharmacol Toxicol Methods 2000; 44(3):453-9.

Enerback L, Lundin P M. Ultrastructure of mast cells in normal and compound 48/80-treated rats. Cell Tissue Res 1974; 150:95-105.

Fukamachi S, Mori T, Sakabe J, Shiraishi N, Kuroda E, Kobayashi M, et al. Topical cholecystokinin depresses itch-associated scratching behavior in mice. J Invest Dermatol 2011; 131(4):956-61.

Greaves M W. Itch in systemic disease: therapeutic options. Dermatol Ther 2005; 18:323-7.

Green A D, Young K K, Lehto S G, Smith S B, Mogil J S. Influence of genotype, dose and sex on pruritogen-induced scratching behavior in the mouse. Pain 2006; 124:50-8.

Han S K, Mancino V, Simon M I. Phospholipase Cbeta 3 mediates the scratching response activated by the histamine H1 receptor on C-fiber nociceptive neurons. Neuron 2006; 52(4):691-703.

Ikoma A, Steinhoff M, Stander S, Yosipovitch G, Schmelz M. The neurobiology of itch. Nat Rev Neurosci 2006; 7:535-47.

Inagaki N, Nakamura N, Nagao M, Musoh K, Kawasaki H, Nagai H. Participation of histamine H1 and H2 receptors in passive cutaneous anaphylaxis-induced scratching behavior in ICR mice. Eur J Pharmacol 1999; 367:361-71.

Inagaki N, Igeta K, Shiraishi N, Kim J F, Nagao M, Nakamura N, et al. Evaluation and characterization of mouse scratching behavior by a new apparatus, MicroAct Skin Pharmacol Appl Skin Physiol 2003; 16:165-75.

Irman-Florjanc T, Erjavec F. Compound 48/80 and substance P induced release of histamine and serotonin from peritoneal mast cells. Agents Actions 1983; 13:138-41.

Ishii I, Kurozumi S, Orito K, Matsuda H. Automatic scratching pattern detection for laboratory mice using high-speed video images. IEEE Trans Automat Sci Eng 2008; 5(1): 176-82.

Jeffry J, Kim S, Chen Z F. Itch signaling in the nervous system. Physiology (Bethesda) 2011; 26(4):286-92.

Johanek L M, Meyer R A, Friedman R M, Greenquist K W, Shim B, Borzan J, et al. A role for polymodal C-fiber afferents in nonhistaminergic itch. J Neurosci 2008; 28(30):7659-69.

LaMotte R H, Shimada S G, Sikand P. Mouse models of acute, chemical itch and pain in humans. Exp Dermatol 2011; 20(10):778-82.

Liu T, Berta T, Xu Z Z, Park C K, Zhang L, LU N, et al. TLR3 deficiency impairs spinal cord synaptic transmission, central sensitization, and pruritus in mice. J Clin Invest 2012; 122(6):2195-207.

Liu Q, Tang Z, Surdenikova L, Kim S, Patel K N, Kim A, et al. Sensory neuron-specific GPCR Mrgprs are itch receptors mediating chloroquine-induced pruritus. Cell 2009; 139(7):1353-65.

Nielsen E H, Clausen J. Electron microscopic study of the regeneration in vivo of rat peritoneal mast cells after histamine secretion. Cell Tissue Res 1982; 224(2):465-8.

Oppenheim A V, Schafer R. Discrete-time signal processing. second ed. New York: Prentice Hall; 1999.

Orito K, Chida Y, Fujisawa C, Arkwright P D, Matsuda H. A new analytical system for quantification scratching behaviour in mice. Br J Dermatol 2004; 150(1):33-8.

Oude Elferink R P, Kremer A E, Martens J J, Beuers U H. The molecular mechanism of cholestatic pruritus. Dig Dis 2011; 29(1):66-71.

Paus R, Schmelz M, Biro T, Steinhoff M. Frontiers in pruritus research: scratching the brain for more effective itch therapy. J Clin Invest 2006; 116:1174-86.

Ringkamp M, Schepers R J, Shimada S G, Johanek L M, Hartke T V, Borzan J, et al. A role for nociceptive, myelinated nerve fibers in itch sensation. J Neurosci 2011; 31(42):14841-9.

Silva L L, Gomes B S, Sousa-Neto B P, Oliveira J P, Ferreira E L, Chaves M H, et al. Effects of Lecythis pisonis Camb. (Lecythidaceae) in a mouse model of pruritus. J Ethnopharmacol 2012; 139(1):90-7 [Epub 2011 Oct. 28].

Shim W S, Tak M H, Lee M H, Kim M, Kim M, Koo J Y, et al. TRPV1 mediates histamine-induced itching via the activation of phospholipase A2 and 12-lipoxygenase. Neuroscience 2007; 27(9):2331-7.

StatSoft, Inc. Electronic statistics textbook. Tulsa, Okla.: StatSoft; 2012, WEB: http://www.statsoft.com/textbook/poweranalysis.

Sugimoto Y, Umakoshi K, Nojiri N, Kamei C. Effects of histamine H1 receptor antagonists on compound 48/80-induced scratching behavior in mice. Eur J Pharmacol 1998; 351(1):1-5.

Umeda K, Noro Y, Murakami T, Tokime K, Sugisaki H, Yamanaka K, et al. A novel acoustic evaluation system of scratching in mouse dermatitis: rapid and specific detection of invisibly rapid scratch in an atopic dermatitis model mouse. Life Sci 2006; 79(22):2144-50.

Yaksh T L, Ozaki G, McCumber D, Rathbun M, Svensson C, Malkmus S, et al. An automated flinch detecting system for use in the formalin nociceptive bioassay. J Appl Physiol 2001; 90:2386-402.

Yuman N, Ishii I, Yamamoto K, Orito K, Matsuda H. Real-time scratching behavior quantification system for laboratory mice using high-speed vision. J Real-Time Image Proc 2009; 4:181-90.

Example 3

Materials and Methods

All studies were performed according to protocols approved by the Animal Care and Use Committee of the University of California San Diego.

Animals

Male Holtzman rats, (250-300 g) obtained from Harlan Sprague Dawley (Livermore, Calif.) were employed in this study. Animals were received and allowed a 7-day period of acclimation prior to being admitted into the study. Rats were multiply housed in standard rodent cages with saw dust bedding, maintained in a 12 h light/dark cycle environment and allowed ad libitum access to water and standard rodent chow. All studies were carried out between 10 AM and 4 PM of the light cycle.

Pruritus Model

Two groups of seven animals were randomly assigned to either the experimental or control treatment. To prepare the animal for treatment, the motion detection band was placed around the hind paw (e.g., over the metatarsals and distal tarsals) ipsilateral to the site of treatment and secured using a drop of cyanoacrylate. The animals were then acclimated in testing chambers for 30 minutes. To induce scratching behavior, the animal was first lightly sedated (Isoflurane 2% in Air, until loss of righting response). The dorsolateral aspect of the neck and upper shoulder was then shaven on the side ipsilateral to the detection band. The pruritogen (48/80) or vehicle (saline) was then administered intradermally in the shaven area using a 30-gauge needle. The animal was then returned to the testing chamber and data acquisition was initiated. All animals were ambulatory within 1-2 minutes. Each experiment had a duration of 30 minutes after the intradermal injection after which the detection band was removed and the animal returned to its habitat.

Drugs

The drug employed in this study was Compound 48/80 (8 mg/mL) (Sigma-Aldrich, St Louis). The drug was prepared for delivery in saline (0.9%) and delivered in a 0.1 mL volume intradermally (ID).

Paw Motion Detector (PMD)

The detection system employs transmitting coils under the Plexiglass test cylinder (15 cm diameter, 35 cm high), which emit a 5-8 mW, 6-8 KHz sinusoidal electromagnetic field (Marino et al 2012). Movement in the electromagnetic field of a small metal band temporarily affixed to the hind paw of the animal subject perturbs the standing wave and generates a signal by the detection coil. (See Yaksh et al 2001 for details of band and chamber description). The raw waveform produced by the motion of the band on the paw of the rat can be saved for later analysis or immediately processed over the course of an experiment. Signal processing includes smoothing the raw data using a moving average, selecting for specific amplitudes of disruption, and specifying the proper frequency of motion associated with an animal scratching. Processed waveforms are then subject to a user-controllable peak detector, which counts the number of wave-peaks which when properly tuned correspond to the number of scratch counts or motions of interest.

Study Protocol

Raw/Unfiltered Data Collection.

To validate the ability of the Paw Motion Detector to detect scratching behavior in Rats, ID injections of the pruritogen Compound 48/80 were performed. To permit follow up analysis, the PMD system recorded the raw data produced by the movement of the rat in the test chamber for 30 minutes. Concurrently, a video recording of the animal's behavior was obtained. A trained observer who catalogued individual scratch counts over time then reviewed the video produced using the criteria described by Kuraishi et al (2005). Observer counting of high frequency motions was aided by the use of slow motion playback. An observer scratch count was defined as the elevation of the ipsilateral hind paw to the site of injection followed by a swiping downward motion across the site of injection. Observer scratch counts were recorded in 1-minute epochs for time course and totaled in 5 and 30-minute intervals for measurement comparisons.

Scratch Analysis.

The, unanalyzed (raw) PMD signal from each rat after ID 48/80 or saline was systematically subjected to a post hoc analysis where in four Algorithm variables were systematically modified. The algorithm variables were: Range Window Length/Convolution length, Peak Width, Frequency Pass-band, and Peak Threshold. A brief description of these variables follows:

Range Window Length/Convolution Length: determines the power of a moving average approximation of the raw signal. By increasing or decreasing this value the experimenter can either smooth or enhance the resolution of the signal passed to the detector algorithm and thereby eliminate noise not associated with animal movement.

Peak Width: the number of samples at 1 kHz required to identify a wave peak (generated by a change in the animal's motion in the Z axis). This was typically held constant at 10 samples as this was the maximum resolution allowed by the software.

Frequency Pass-band: sets the minimum and maximum frequency of the waveform generated by the animal's motion passed to the detector algorithm. This pass-band allows the experimenter to select for high or low frequency motions and attenuates motions generated outside the pass-band. This is a new feature of the PMD signal conditioning system, and allows for greater accuracy in regards to the actual identity of the animal motion generating the waveform.

Peak Threshold: catalogues wave-peaks as having a large enough magnitude to be counted. Once the signal passes through the above filters and the peak meets or exceeds threshold, it can be associated with a scratch (or other selected for motion) when the algorithms are properly tuned. Peaks meeting threshold are then logged and available for export at the end of the experiment. Thus, each raw signal from each animal was run through the PMD algorithms to provide a minute by minute machine scratch count as defined by a specified algorithm.

Algorithm Validation.

The machine count was then compared to the minute by minute scratch count analysis of the same animal by the human observer. These data sets could then be analyzed: i) as total machine and observer scratch counts for a 30 min epoch; or, ii) plotted as a regression line (human observer count vs. machine count) for each 5 min epoch for each rat using the specified algorithm. Candidate machine detection algorithms providing data with regression slopes approximating 1, Y intercepts approximating zero, and higher correlation ($r^2$) coefficients were considered to be superior to algorithms with regression slopes greater (over-counting) or lesser (under-counting as compared to the human observer), higher levels of scratching when the human observer observed no scratching (e.g. Y intercept≠0) and lower correlation ($r^2$) coefficients. A variety of PMD scratch analysis filters were evaluated and their output counts compared to human observer counts in order to find an optimal algorithm configuration to describe ID 48/80 induced rat scratching.

Power Analysis.

To establish the minimum number of animals required to show significance of difference in incidence of scratching otherwise produced by intradermal 48/80 after a drug treatment, a power analysis was undertaken using the standard method facilitated by web based software (DSS Research, Ft. Worth, Tex.).

Results

Human Observation Counts

Figure 10:
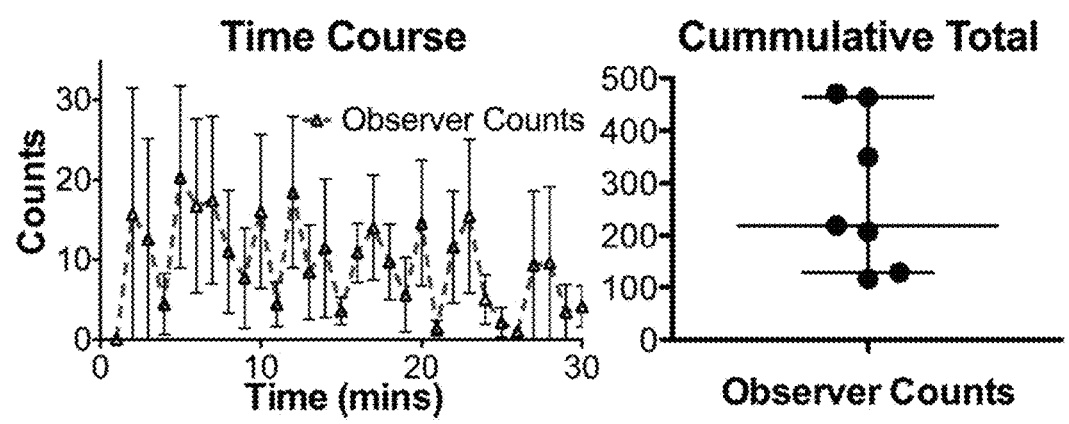
FIG. 10. Visually reported scratch counts over 30 minutes. Following ID injection of Compound 48/80, video recordings captured animal behavior over 30 minutes. Video playback review by a trained observer reports scratch counts plotted against time (n=7 Mean SEM).

After injection with Compound 48/80 (0.8 mg/0.1 mL) in the lower portion of the neck just above the shoulder, trained observer analysis of the generated video recordings showed consistent homotopic scratching at the injection site with the ipsilateral hind paw. This scratching behavior persisted in periodic bursts through approximately 30 min (FIG. 10). The morphology of this scratching behavior was consistent with that reported by other investigators after Compound 48/80 induced scratching (Kuraishi et al, 1995; LaMotte et al, 2011). Cumulative counts after ID 48-80 was 279±57 (N=7, mean±SEM), respectively.

PMD Scratch Analysis

Using the raw data recorded using the PMD after the experimental injection of compound 48/80 into the rostral portion of the back, detector-algorithm parameters were modulated to select for the waveform to be counted when the rat scratched. Table 2 lists five representative algorithms in which these different parameters were systematically varied. The minute by minute counts reported by these several machine algorithms in the 48/80 group and the observer counts (obtained from the concurrent video analysis) plotted over the 30 min data collection interval are presented in FIG. 11.

TABLE 2

Machine algorithm configurations used to analyze scratch behavior*

| | | Samples Algorithm Configurations Tested | | | | |
|---|---|---|---|---|---|---|
| | | R1-22 | R1-31 | R1-24 | R1-25 | R1-32 |
| Results of Linear Regression of Machine vs. Observer Counts | Slope + SEM | 0.4134 ± 0.04590 | 0.202 ± 0.189 | 1.009 ± 0.06935 | 1.439 ± 0.1488 | 1.93 ± 0.172 |
| | y-intercept | 8.65 ± 3.16 | 17.6 ± 13.0 | 2.27 ± 4.78 | 6.92 ± 10.2 | 39.6 ± 11.8 |
| | $R^2$ | 0.6331 | 0.0238 | 0.8182 | 0.6658 | 0.729 |
| Algorithm Parameters* | Range Window Length (samples) | 150 | 76 | 76 | 20 | 76 |
| | Convolution Length (samples) | 150 | 76 | 76 | 20 | 76 |

TABLE 2-continued

Machine algorithm configurations used to analyze scratch behavior*

|  |  | Samples Algorithm Configurations Tested | | | | |
| --- | --- | --- | --- | --- | --- | --- |
|  |  | R1-22 | R1-31 | R1-24 | R1-25 | R1-32 |
| Band-pass Filter | High Cutoff (Hz) | 25 | 30 | 25 | 25 | 20 |
| Settings | Low Cutoff (Hz) | 15 | 20 | 15 | 15 | 10 |
|  | Order | 2 | 2 | 2 | 2 | 2 |

*The following algorithm parameters and their respective values were held constant for the above configurations: Acquisition Rate (1 Khz), DAQ Buffer Size 5000(samples), Peak Threshold (0.2 Volts), Peak Width (10 Samples).
*Previous motion and video recordings of rats treated with ID Compound 48/80 were analyzed with various algorithm configurations and the results were compared to video playback observations in a linear regression (see FIG. 10). As indicated: algorithms R1-22, and R1-32 undercounted, configurations R1-25 and R1-32 over counted, and configuration R1-24 was the most accurate.

Regression of Observer and PMD Scratch Counts

Figure 11:
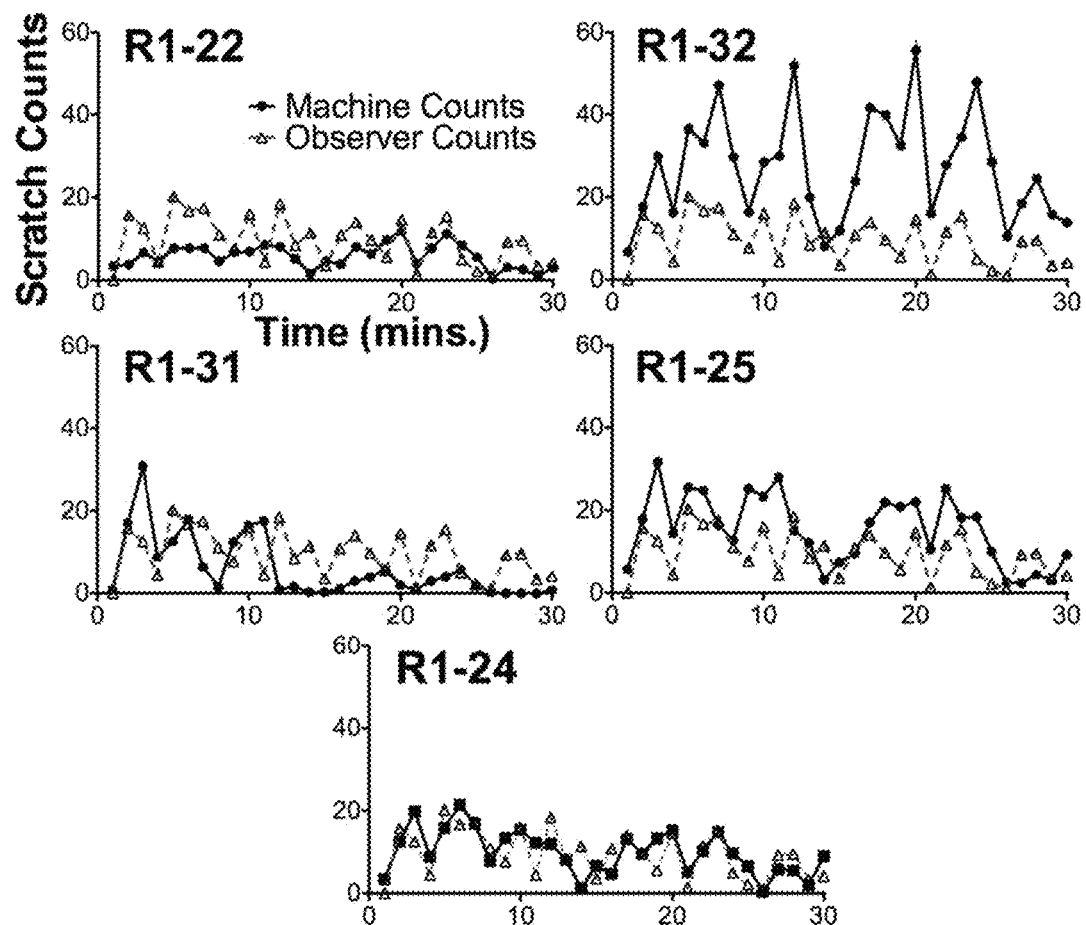
FIG. 11. Visually reported and Machine Assessed Scratch Counts over 30 minutes. Following ID injection of Compound 48/80, video and ANA recordings captured movement over 30 minutes. Machine algorithm analysis of scratch counts was then performed using various algorithm configurations and compared with visual observation. Note: Y axes are varied. See Table 1 for algorithm configurations.
Figure 12:
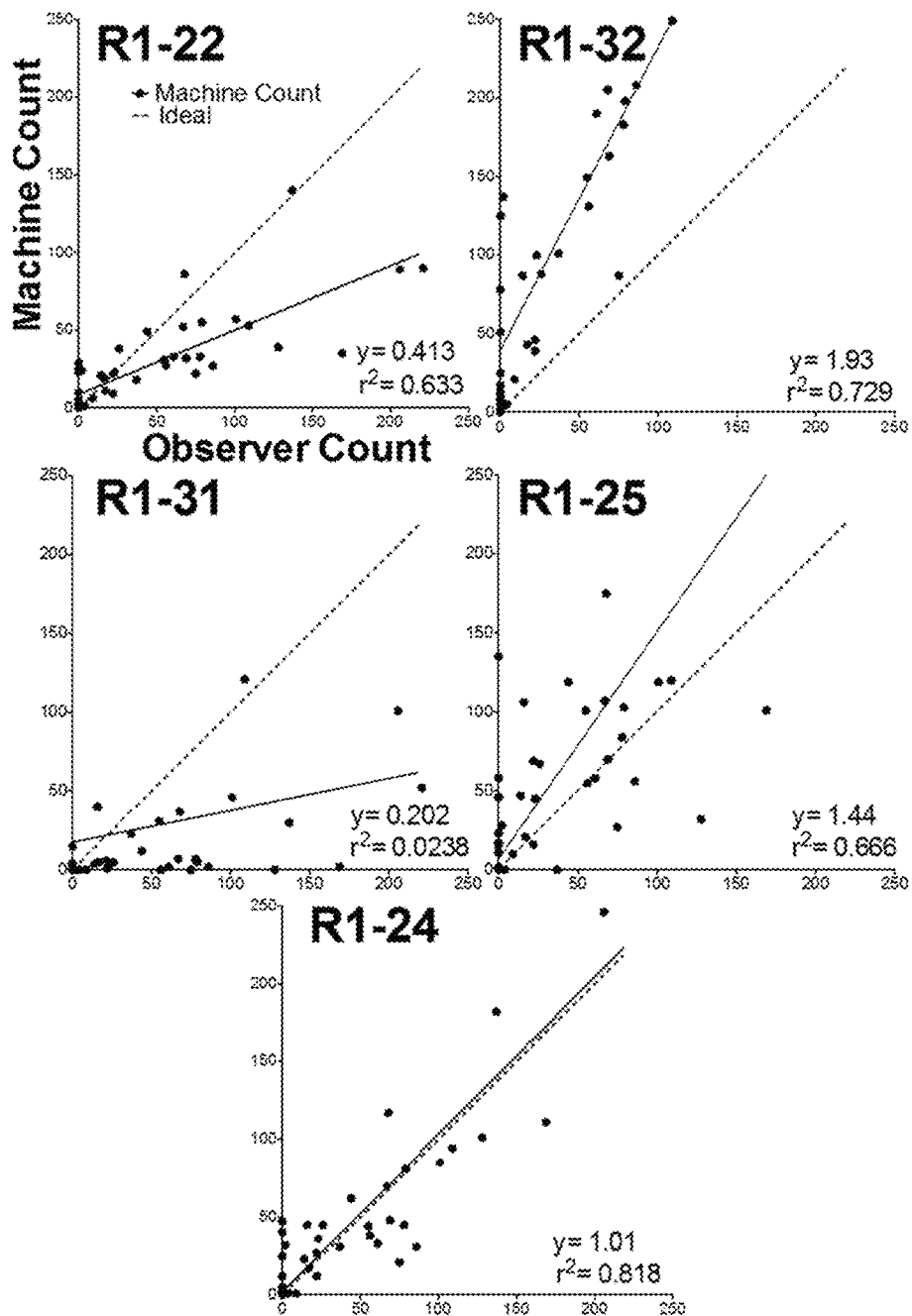
FIG. 12. Linear Regression of machine algorithm scratch counts versus video playback observation. Previously recorded scratch behavior of 7 rats treated with ID Compound 48/80 [8 mg/ml]×0.1 ml over thirty minutes using the ANA was analyzed with various count-algorithm configurations. Each point represents the observed (X) and machine (Y) scratch count at a given time point. A slope of 1 represents concurrence between machine reported and visually reported scratch behavior. Analysis with algorithm R1-24 produced a slope of 1.01±0.0694 $r^2$=0.818. See Table 1 for algorithm configuration specifics.

To provide a quantifiable index of the degree to which the machine counts reported by the several algorithms shown in FIG. 11 matched the human observer counts, Human observer and PMD algorithm configuration scratch counts were summed into six 5-minute intervals representing the thirty-minute experiment for each rat. Linear regressions were then generated comparing observer counts for each 5-minute interval with machine counts obtained with a given algorithm for the same intervals. FIG. 12 plots the regression lines for the analysis of the individual data processed by the several algorithms. The calculated best-fit regression lines of the population rat data were used as a measure of algorithm configuration accuracy. The parameters for these regression analyses are presented in tabular form in Table 2. As can be seen, the several algorithms differ in their slope from 0.2 (under counting) to 1.93 (over counting); Y-intercepts ranging from 2.3 to 39.6 and $r^2$ values ranging 0.02 to 0.82 (Table 2). As indicated in Table 2 and FIG. 12, the algorithm configuration R1-24 yielded a slope of 1.009±0.069 (mean±SEM), the highest $r^2$ (0.82) and a Y-intercept near zero (Y=2.3±4.8; mean±SEM) over a wide range of scratching intensities between the machine and observer counts, indicating that this algorithm displayed the best analytic configuration amongst the algorithms examined. (FIG. 12).

Machine Counts for ID Vehicle Versus ID 48/80

Figure 13:
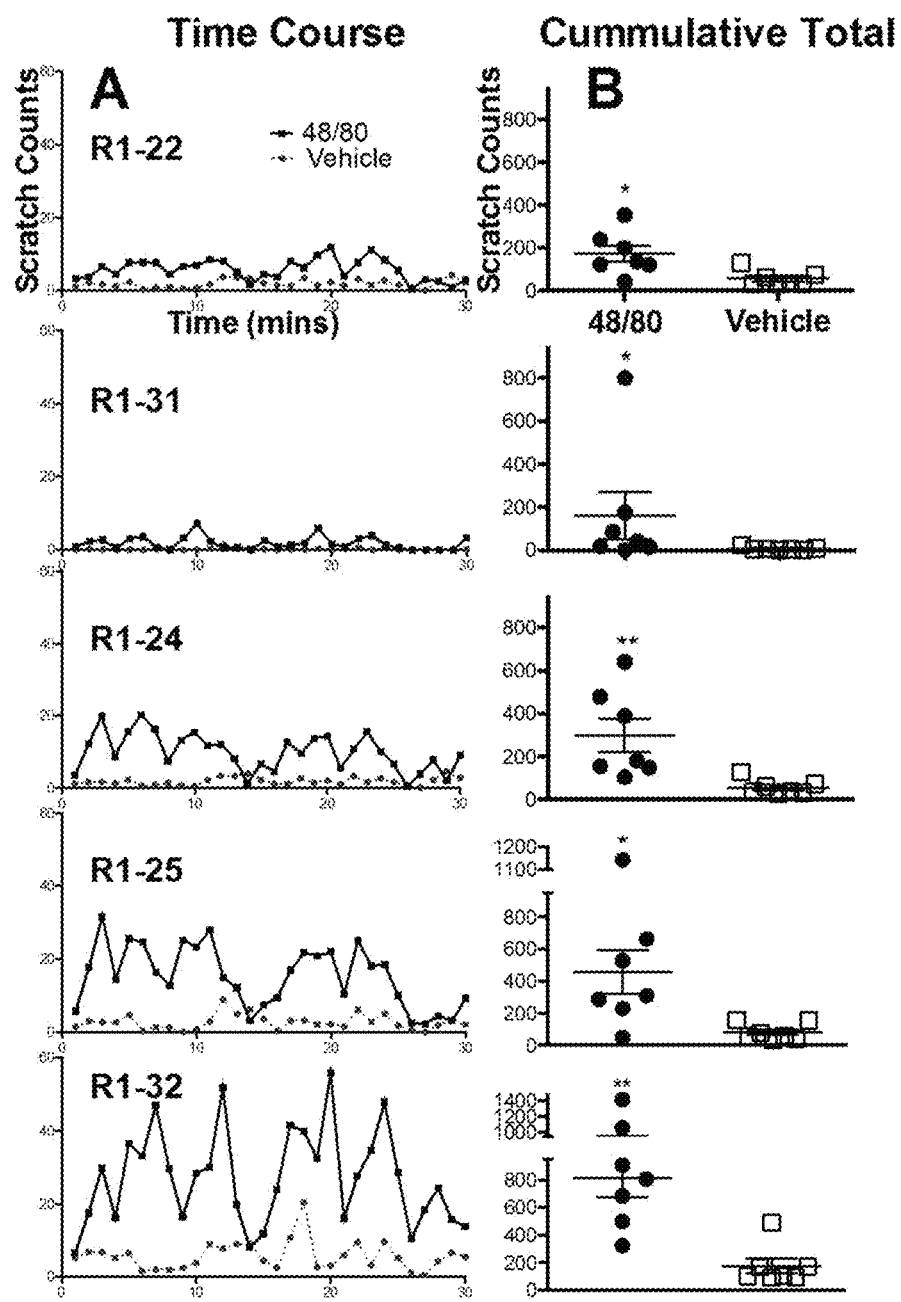
FIG. 13. Machine Algorithm Assessment of Compound 48/80 induced Pruritus over 30 minutes. Rat scratch behavior was recorded over 30 minutes post ID Compound 48/80 (8 mg/ml) n=7 or Vehicle n=7. Various analysis algorithm configurations (each row) were then employed to analyze scratch counts. (A) Mean scratch count time course of ID 48/80 or Vehicle (n=7 for both groups) as analyzed by 5 different algorithm configurations. (B) Cumulative total scratch counts in 30 minutes of ID Compound 48/80 n=7 and vehicle treated rats n=7 as analyzed by 5 different algorithm configurations. Bars represent Mean, SEM (note Y axis scale is not constant). * p<0.05 vs. vehicle.

FIG. 13 presents the time course and total 30 min counts after ID vehicle and ID 48/80 for the machine counts using the several algorithm configurations. The regression plot indicated that the R1-24 configuration provided the optimal human observer covariance. As indicated, this algorithm yielded vehicle scratch counts of 56±13 versus 298±78 for ID 48-80 (p<0.05).

Power Analysis

A power analysis to determine the minimum group size needed to establish statistically significant change was performed using the machine counted mean and SEM of 298.6±77.61 after ID 48/80. Table 3 illustrates the number of animals required to show varying degrees of reversal when one is screening an anti-pruritogen for a statistically significant reversal (e.g. p<0.05). For example, calculated with a B=0.20 and an alpha=0.05, robust effects, like a 70% reduction, can be determined with 6 animals

TABLE 3

Summary of Power analysis indicating number of rats required to demonstrate that different % reductions in scratching behavior after intradermal Compound 48/80*

| Reduction | Sample Size Required |
| --- | --- |
| 30% | 32 |
| 50% | 12 |
| 70% | 6 |

*Calculated based on α: p < 0.05; β: 0.8

Discussion

Pruritus arises from a variety of clinical pathologies and can, without question, lead to a marked diminishment in the quality of life of the sufferer. In the extreme, this pruritus can produce clinical conditions with important impact upon patient welfare. As reviewed, the strategies to treat pruritus are limited. Assessment of scratching in preclinical rodent surrogate models is an important component in advancing our ability to achieve an understanding of the physiology and pharmacology of pruritus and to develop agents to treat this symptom. An important limitation in the field is the issue of assessing quantitatively the scratching response initiated by intradermal pruritogens.

The present work describes the application of a model to assess unilateral paw movement. The present automated detection system was first developed to detect hind paw flinching for the assessment of antinociceptive agents (Yaksh, et al, 2001). The systems permitted the definition of hind limb flinching of the rat's paw initiated by intraplantar formalin. The advantages of this system are the use of a minimally invasive light weight band, the lack of restraint of the animal, and the ability to detect movement of a single paw. It is most useful to note that a simple detection algorithm permitted a high level of certainty that the phenotypic flinch response of the injected paw could be readily detected with minimum contribution of gross movement.

When the model was applied to assess scratching in the rodent, the morphology of the behavior, where in the paw was elevated and animals exhibited sequences of high frequency bursts, led to the flinch algorithm reporting a high level of activity in the non-scratching mouse. Ensuing work to address this problem led to the development of the mouse algorithm (Marino, et al 2013). The invention provides validation of yet another scratch detection algorithm in an attempt to provide scratching detection that paralleled the trained human observer. The specific algorithm employed revealed a highly significant covariance between the scratch counts as measured by a trained human observer and machine counts. Thus, the slope of the population regression line (machine vs. human counts) revealed a slope not different from 1 with an $r^2$ value showing a high level of goodness of fit and a close covariance. Importantly, the Y-intercept was zero emphasizing that in the absence of observed scratch counts, the machine counts were not picking up non scratching activity manifested by the rat.

An important variable is the issue of power. As noted on the basis of these data, when screening agents for anti pruritic activity, the initial aim may be to define agents with a high degree of activity. In this case, prominent inhibition (e.g. a 70% reduction) may be an appropriate criterion and on that basis screening could be usefully achieved with 6 rats. Higher certainty or acceptance of smaller changes would predictably require larger groups (e.g. a 50% reduction would require 12 rats based on the present power analysis).

There are two important advantages to automated systems. First, the automated system reduces the contribution to variation accrued by the use of several human observers in a given study and the stability of the observations over time. While videotaping allows multiple reviews of the same data, many studies do not make it clear whether all work was done a single individual over time or the consensus of several individuals on a single reading. A second important advantage of these systems is the time required to train individuals to become competent and reliable observers. The use of automated detection systems require that the individual achieve competency in handling an animal and delivering the ID injections.

These studies thus provide validation of the rat system and suggest that such automated scratch detection and analysis can be useful in detecting pruritic behavior and facilitate the screening of antipruritic agents.

What is claimed is:

1. A method for automated assessment of pruritus, comprising:
    (a) detecting movement and movement frequency of a nonferrous metal band located on a limb of a subject animal so as to obtain a signal and plurality of signals associated with the detection movement, wherein the signal and plurality of signals are obtained by detecting perturbations within an electromagnetic field from the movement and movement frequency of the metal band in the electromagnetic field;
    (b) processing the signal and plurality of signals associated with the detected movement through a first algorithm configured to distinguish a scratch movement from an ambulatory movement, thereby establishing a scratch movement trigger;
    (c) translating the processed scratch movement trigger signal into scratch counts by using a second algorithm that registers a scratch count as being 1 or 2 scratch movement triggers in a time period from 0.5 to 1.5 seconds; and
    (d) processing the scratch counts using a third algorithm that determines scratch count clusters over a time course.

2. The method of claim 1 further comprising transforming said scratch counts into macrobursts.

3. The method of claim 2, wherein said scratch counts are transformed into macrobursts through an algorithm configured to establish a macroburst.

4. The method of claim 1, wherein the third algorithm is a fast Fourier transform algorithm.

5. The method of claim 2, wherein the macrobursts define and quantify the itch-scratch-quiescence cycle in pruritic animals.

6. The method of claim 1 further comprising storing scratch movement triggers onto a storage medium.

7. The method of claim 1 further comprising storing scratch counts onto a storage medium.

8. The method of claim 3 further comprising storing macrobursts onto a storage medium.

9. The method of claim 2 further comprising analyzing macroburst patterns to study integration of pruritic input within a neural axis.

10. The method of claim 1, wherein the band is a nonrestrictive and lightweight band.

11. The method of claim 1, wherein the band comprises a electromagnetically-sensitive material.

12. A method for determining whether an agent induces pruritus in a subject comprising:
    (a) applying the agent suspected of inducing pruritus to the subject at a predetermined area;
    (b) detecting movement and movement frequency of a nonferrous metal band located on a limb of a subject animal so as to obtain a signal and plurality of signals associated with the detection movement, wherein the movement is a scratch movement to the predetermined area on the subject, wherein the signal and plurality of signals are obtained by detecting perturbations within an electromagnetic field from the movement and movement frequency of the metal band in the electromagnetic field;
    (c) processing the signal and plurality of signals associated with the detected movement through an algorithm configured to distinguish a scratch movement from an ambulatory movement, thereby establish a scratch movement trigger;
    (d) translating the processed scratch movement trigger signal into scratch counts by using a second algorithm that registers a scratch count as being 1 or 2 scratch movement triggers in a time period from 0.5 to 1.5 seconds; and
    (e) comparing the generated scratch counts to those generated from a nonpruritic agent, an increase indicating that the agent induces pruritus.

13. A method for determining whether an agent reduces pruritus comprising: (a) determining whether a potential pruritogen induces pruritus by the method of claim 1; (b) mixing the agent with the pruritogen in varying amounts and repeating the method of claim 1; (c) comparing the generated scratch counts to determine relative reduction of pruritic activity.

14. The method of claim 1, wherein the limb is a hind limb paw or a fore limb paw of a subject animal.

15. The method of claim 14, wherein the subject animal is a mouse, rat, squirrel, guinea pig, hamster, rabbit, shrew, mole, mink, cat or dog.

16. A method for determining whether an agent induces pruritus in a subject comprising:
    (a) attaching a band to a limb of said subject;
    (b) attaching a signal detection and processing device to the subject, the device being operatively connected to a memory device capable of storing retrieved signals, the device being able to detect motion of the band on the subject;
    (c) detecting movement of the band on the subject that has been administered with the agent so as to obtain a signal or plurality of signals associated with the detection movement, wherein the movement is a scratch movement to a predetermined area to which the agent has been administered on the subject;
    (d) processing the signal and plurality of signals associated with the detected movement through a first algorithm configured to distinguish a scratch movement from an ambulatory movement, thereby establishing a scratch movement trigger;
    (e) translating the processed scratch movement trigger signal into scratch counts by using a second algorithm that registers a scratch count as being 1 or 2 scratch movement triggers in a time period from 0.5 to 1.5 seconds; and
    (f) processing the scratch counts using a third algorithm that determines scratch count clusters over a time course; and (g) comparing the generated scratch counts to those generated from a nonpruritic agent, an increase indicating that the agent induces pruritus;

wherein the signal detection and processing device comprises a processor configured to perform the steps (d)-(f).

17. The method of claim 1, wherein the electromagnetic field is generated by a transmitting antenna comprising an electromagnetic transmitting coil.

18. The method of claim 17, wherein perturbations within an electromagnetic field are detected by a receiving antenna comprising an electromagnetic receiving coil.

19. The method of claim 18, wherein the electromagnetic transmitting coil and the electromagnetic receiving coil are circular and concentric, and wherein the diameter of the electromagnetic transmitting coil is smaller than the diameter of the electromagnetic receiving coil.

20. The method of claim 1, wherein the scratch count clusters are determined over a 60-minute time course by using a number of scratch counts per minute.

* * * * *